USO11913077B2

United States Patent
Reynolds et al.

(10) Patent No.: US 11,913,077 B2
(45) Date of Patent: Feb. 27, 2024

(54) COMPOSITIONS AND METHODS FOR THE DIAGNOSIS AND TREATMENT OF ALT CANCER

(71) Applicant: Texas Tech University System, Lubbock, TX (US)

(72) Inventors: Charles Patrick Reynolds, Lubbock, TX (US); Balakrishna Koneru, Lubbock, TX (US); Shawn Macha, Lubbock, TX (US)

(73) Assignee: Texas Tech University System, Lubbock, TX (US)

( * ) Notice: Subject to any disclaimer, the term of this patent is extended or adjusted under 35 U.S.C. 154(b) by 685 days.

(21) Appl. No.: 16/979,364

(22) PCT Filed: Mar. 9, 2019

(86) PCT No.: PCT/US2019/021502
§ 371 (c)(1),
(2) Date: Sep. 9, 2020

(87) PCT Pub. No.: WO2019/173806
PCT Pub. Date: Sep. 12, 2019

(65) Prior Publication Data
US 2021/0002730 A1  Jan. 7, 2021

Related U.S. Application Data

(60) Provisional application No. 62/641,218, filed on Mar. 9, 2018.

(51) Int. Cl.
*C12Q 1/6886* (2018.01)
*A61K 31/198* (2006.01)
*A61K 31/439* (2006.01)
*A61K 45/06* (2006.01)
*A61P 35/00* (2006.01)

(52) U.S. Cl.
CPC .......... *C12Q 1/6886* (2013.01); *A61K 31/198* (2013.01); *A61K 31/439* (2013.01); *A61K 45/06* (2013.01); *A61P 35/00* (2018.01); *C12Q 2600/156* (2013.01)

(58) Field of Classification Search
IPC ................ C12Q 1/6886; A61K 31/198,31/439, 45/06; A61P 35/00
See application file for complete search history.

(56) References Cited

U.S. PATENT DOCUMENTS

| 2005/0090540 A1 | 4/2005 | Bykov et al. |
| 2014/0364460 A1 | 12/2014 | Freed-Pastor et al. |
| 2017/0198337 A1 | 7/2017 | Silva et al. |

FOREIGN PATENT DOCUMENTS

| CN | 103585618 A | * | 2/2014 | |
| WO | WO-2008020653 A1 | * | 2/2008 | ........... C12N 15/113 |
| WO | WO-2011089234 A2 | * | 7/2011 | ........... A61K 31/439 |
| WO | WO-2017029498 A1 | | 2/2017 | |
| WO | WO-2017159877 A1 | | 9/2017 | |
| WO | WO 2018/035200 | | 2/2018 | |

OTHER PUBLICATIONS

Min (Nucleic Acids Research vol. 45 pp. 2615-2628. Published online Jan. 13, 2017) (Year: 2017).*
Deeg (Frontiers in Oncology vol. 6 article 186 published online Aug. 2016), (Year: 2016).*
Komiya (J. Orthop Res vol. 16 pp. 15-22 published 1998) (Year: 1998).*
The International Search Report and Written Opinion for PCT/US2019/021502, dated May 24, 2019.
The International Preliminary Report on Patentability for PCT/US2019/021502, dated Sep. 24, 2020.
Heaphy CM, de Wilde RF, Jiao Y, et al. Altered telomeres in tumors with ATRX and DAXX mutations. Science. 2011;333(6041):425. doi:10.1126/science.1207313.
Koneru, B., et al., ALT neuroblastoma chemoresistance due to telomere dysfunction-induced ATM activation is reversible with ATM inhibitor AZD0156, Science Translational Medicine Aug. 18, 2021: vol. 13, Issue 607, eabd5750, DOI: 10.1126/scitranslmed. abd5750.
Search Report for EPO Application No. 19763624.4, dated Jan. 27, 2022.
Fogli et al., Detection of alternative lengthening of telomeres pathway in malignant gliomas for improved molecular diagnosis. J Neurooncol, 2017, 135:381-390.
Macha et al., "Alternative Lengthening of Telomeres in Cancer Confers a Vulnerability to Reactivation of p53 Function." Cancer Res. Sep. 16, 2022;82(18):3345-3358.
Koneru et al., "ALT neuroblastoma chemoresistance due to telomere dysfunction-induced ATM activation is reversible with ATM inhibitor AZD0156." Sci Transl. Med. Aug. 18, 2021;13(607).
Cancer Discovery Research Watch entitled "ATM Inhibition Sensitizes ALT Neuroblastomas To Chemotherapy." Cancer Discov, 2021; 11:2368. Published Online on Aug. 27, 2021.

* cited by examiner

*Primary Examiner* — Theodore R. Howell
*Assistant Examiner* — George W Kosturko
(74) *Attorney, Agent, or Firm* — Shackelford, Bowen, McKinley & Norton, LLP

(57) ABSTRACT

A method of treating a cancer in a patient includes obtaining a sample from the patient, using a C-circle assay to detect a presence of an alternative lengthening of telomeres (ALT) phenotype in the sample, and administering an effect amount of at least one of PRIMA-1 or APR-246 to the patient.

23 Claims, 20 Drawing Sheets

COMPOSITIONS AND METHODS FOR THE DIAGNOSIS AND TREATMENT OF ALT CANCER

CROSS-REFERENCES TO RELATED APPLICATIONS

This Application claims priority to U.S. Provisional Patent Application No. 62/641,218, filed on Mar. 9, 2018. The entirety of the aforementioned application is incorporated herein by reference as if fully set forth herein.

TECHNICAL FIELD OF THE INVENTION

The present invention relates in general to the field of cancer therapy, and specifically to the identification and treatment of cancers in which cells exhibit the Alternative Lengthening of Telomeres (ALT) phenotype.

BACKGROUND

Neuroblastoma (NB) is a malignant sympathetic nervous system tumor that accounts for ~8% of childhood cancers. Low-stage patients have a favorable outcome, and stage 4S patients (metastatic disease without bone lesions) in infants can undergo spontaneous regression (without chemotherapy) and generally have excellent clinical outcomes. Spontaneous regression of stage 4S neuroblastoma is thought to be triggered by telomere erosion due low/negative telomerase expression.

High-risk NB, defined by age, stage, and MYCN oncogene amplification, poses a major therapeutic challenge. Outcome for high-risk NB patients can be improved by employing myeloablative therapy followed by maintenance therapy to treat minimal residual disease with the differentiation inducer 13-cis-retinoic acid (13-cis-RA). The Children's Oncology Group expanded on this principle by adding immunotherapy to 13-cis-RA maintenance therapy, but >40% of high-risk NB patients still die of progressive disease. As cytoreduction with DNA damaging agents is critical to success in therapy of high-risk neuroblastoma, understanding mechanisms of therapy resistance and identifying novel therapies to overcome drug resistance are needed to further improve outcome. p53 loss-of-function (often due to TP53 mutation) and increased glutathione (GSH) have been identified as mechanisms of drug resistance, and shown that the GSH synthesis inhibitor BSO has promise in clinically reversing drug resistance in neuroblastoma. A resource lab for the Children's Oncology Group (COG), the ALSF/COG Childhood Cancer Repository is located at TTUHSC (www.COGcell.org). The repository establishes, banks, and distributes world-wide patient-derived cell lines and patient-derived xenografts (PDXs) from childhood cancers. The repository has established cell lines and PDXs from most types of childhood cancer, but the largest panel of models established are from neuroblastoma.

Telomeres are nucleoprotein complexes found at eukaryotic chromosome ends that are essential for maintaining genomic stability. Human telomeres are hexameric $(TTAGGG)_n$ repetitive sequences present at the terminal ends of chromosomes, generally 6-8 kilobases long. Telomeres protect the terminal regions of chromosomes from erosion of coding DNA sequences as a result of the "end replication problem", which is the inability of DNA polymerase to replicate lagging strands completely. In normal somatic cells, telomeres shorten (approximately 50-100 bp per division) with every cell division due to the end replication problem, which eventually triggers p53-dependent cellular senescence, and this acts as a barrier to unlimited cellular proliferation and tumorigenesis.

Another major function of telomeres is protecting the ends of the linear chromosomes from being recognized as DNA strand breaks (i.e., as DNA damage). Telomeric sequences end as a 3' single-stranded overhang that folds back to generate a secondary structure called a telomere loop (t-loop). T-loops, along with the presence of shelterin (6-protein-complexes), cap the telomeres and resolve the end protection problem. It is well-established that telomeric repeat binding factor 2 (TRF2) represses the double-strand break (DSB) repair pathway by inhibiting ATM kinase, and protection of telomeres 1 protein (POT1) prevents activation of the single strand break (SSB) repair pathway by inhibiting ATR kinase activation. Shortening of telomeres during cell growth disrupts the t-loop and results in DNA damage response (DDR) machinery recognizing chromosome ends as a DSB or SSB and activating of ATM/ATR kinases (and p53), which leads to cellular senescence. This process, termed telomere dysfunction, can also occur if shelterin complexes are disrupted from the telomeres leading to DNA damage recognition factors such as 53BP1 and Y-H2AX being co-localized to telomeres.

Unlimited proliferation of cells requires that they maintain telomeres to counter the "end replication" problem. Cells that do not maintain telomeres can only grow for about 50 population doublings as telomere shortening leads to an event known as "crisis" where the cells senesce and eventually die Immortalization of cells (and escape from crisis) requires genetic and/or epigenetic changes that activate an effective telomere maintenance mechanism. Enabling replicative immortality by activating a telomere lengthening mechanism (TMM) is one of the six classic hallmarks of cancer. Most cancer cells, stem cells, and germ cells maintain their telomeres by expressing telomerase, a holoenzyme containing a catalytic protein component with reverse-transcriptase activity encoded by the TERT gene, and an RNA template molecule (hTR) that is encoded by the TERC gene. Telomerase adds telomeric repeats (TTAGGG in humans) to the ends of chromosomes. When assessed for telomerase activity, it was revealed that approximately 85% of tumors maintain their telomere lengths by expressing telomerase and increased telomerase activity was associated with poor prognosis in the majority of human cancers.

About 15% of all cancers (and higher fractions of certain cancers) maintain telomeres without telomerase activity by what is known as "alternative lengthening of telomeres (ALT)". The molecular mechanism of ALT are unclear and the phenotype may represent several mechanisms. The ALT phenotype is characterized by: 1) high telomere content, 2) heterogeneity in telomere length, 3) presence of ALT-associated PML bodies (APB's) containing telomeric repeats, telomere-associated proteins, and proteins involved in DNA repair, recombination, and replication, 4) telomeric c-circles which are partially double-stranded telomeric DNA segments that are highly specific for ALT cells, 5) high rates of telomere sister chromatid exchange (T-SCE), and 6) high frequency of mutations in alpha thalassemia/mental retardation x-linked (ATRX) and/or death domain-associated protein (DAXX). ALT cells have been observed that use HR-dependent DNA replication of telomeres and also undergo post-replicative T-SCE (exchanging telomere DNA from one sister chromatid to the other). It has been proposed that due to unequal T-SCE, ALT cells may incur telomere length changes or acquire extended proliferative capacity. Recent studies have shown that ALT cell lines manifest telomere dysfunction, which has been associated with ATRX loss-of-function (by mutation).

Low telomerase activity is associated with good clinical outcome in NB. It was perplexing that a subset of tumors with poor outcome had long telomeres and low telomerase activity (presumably ALT). Studies of telomerase activity and telomere length, or the scoring of ALT-associated promyelocytic leukemia bodies (APB's) in NB, suggested that approximately 20% of NB tumors potentially had the ALT phenotype. ALT in NB was associated with a lack of MYCN genomic amplification, elongated telomeres, often came from patients of older age at diagnosis, and these patients had a poor clinical outcome. Whole genome sequencing (WGS) of tumors from forty patients with metastatic NB (enriched for older patients) showed somatic mutations in the ATRX gene in 25% of tumors; eight of the ATRX-mutated tumors (and one ATRX-wt) had increased telomere content (TC) and a large ultra-bright telomere fluorescence in-situ hybridization (FISH) signal indicative of ALT. A COG/NCI TARGET study sequenced 240 high-risk NB tumors from patients >18 months of age with metastatic disease at diagnosis by whole-exome sequencing (WES) and WGS. In the COG study ATRX was found to be the most frequently mutated or deleted gene (9.6% of the 240 cases had ATRX aberrations); DAXX mutations were not observed. Neither of these sequencing studies assessed telomerase activity or an ALT-specific marker (ex., c-circles).

SUMMARY

An embodiment of the claimed invention is directed to a method of treating a cancer in a patient, the method comprising: obtaining a sample from the patient; using a C-circle assay to detect a presence of an alternative lengthening of telomeres (ALT) phenotype in the sample; and administering an effect amount of at least one of PRIMA-1 or APR-246 to the patient (alone or in combination with other agents).

A further embodiment of the claimed invention is directed to a method of treating a cancer in a patient, the method comprising: administering at least one of PRIMA-1 or APR-246 in combination with buthinonine sulfoximine to the patient; and wherein the cancer comprises an alternative lengthening of telomeres (ALT) phenotype.

Neuroblastoma provides a unique cancer for studying the role of changes that lead to inactivation of p53, such as TP53 inactivating mutations. This is because, unlike many other cancers, neuroblastomas at diagnosis and before therapy most frequently are p53 functional and there is a very low incidence of TP53 mutations. However, the incidence of p53 loss-of-function (often by TP53 mutation) increases in progressive disease after therapy. Because PRIMA-1 was developed as a drug that could restore p53 function to tumors with TP53 mutations, we assessed the activity of PRIMA-1 in neuroblastoma cell lines. Our panel of neuroblastoma cell lines includes p53-functional cell lines and those that have p53 loss-of-function and lines with TP53 mutations. The panel includes cell lines with TP53 mutations that are telomerase-positive (high TERT expression) and also TERT-low ALT (C-circle-positive) cell lines.

Testing has determined that the activity of PRIMA-1 was significantly greater in ALT neuroblastoma cell lines than it was in TP53-mutated non-ALT neuroblastoma cell lines. Testing was extended to examine ALT cell lines from cancers other than neuroblastoma, and it was observed that all ALT cell lines examined to date are highly sensitive to PRIMA-1. As the literature suggests that both hypoxia and glutathione (GSH) depletion (which can be achieved with the drug buthionine sulfoximine (BSO), we tested activity of PRIMA-1 combined with BSO and also in hypoxia and compared ALT to non-ALT cancer cell lines, and that high activity against ALT cancer is increased in hypoxia and by combining PRIMA-1MET with BSO.

Because only a subset of TP53-mutated cancers are sensitive to PRIMA-1, having a biomarker that identifies patients who may have a very high response rate to the drug is valuable for not only enriching for clinical responses in a registration-seeking clinical trial, but can be employed to guide the clinical use of the drug. Having identified highly-responsive populations based on a biomarker is a stated goal by the FDA as the preferred route for drug development. Moreover, identifying a biomarker for a highly responsive population that goes across cancer histologies can lead to an FDA approval for treating that phenotype, rather than a particular cancer histology. An example of this approach is the recent approval granted by FDA for treating patients with the molecular phenotype of microsatellite instability (MSI) with Keytruda®, regardless of the cancer histology. The current approach of the FDA to anti-neoplastic drug development and marketing approval makes having a robust biomarker as a companion to a new agent "the holy grail" of drug development, markedly decreasing the costs of obtaining an FDA registered indication and enabling the indication to be applicable to a larger market as the registered indication is not limited to a single cancer histology.

Various illustrative embodiments are disclosed below:

Use of PRIMA-1, APR-246, and related compounds and derivatives (alone or in combination with DNA damaging agents) for treating cancers with the alternate telomere lengthening (ALT) phenotype, regardless of TP53 mutation status or histological type.

Use of the C-circle assay to identify cancers that will be highly sensitive to PRIMA-1, APR-246, and/or related compounds and derivatives, alone or in combination with DNA damaging agents.

Use of PRIMA-1, APR-246, and related compounds and derivatives (alone or in combination with DNA damaging agents) for treating neuroblastomas that are C-circle positive.

Use of PRIMA-1, APR-246, and related compounds and derivatives (alone or in combination with DNA damaging agents) for treating osteogenic sarcomas that are C-circle positive.

Use of PRIMA-1, APR-246, and related compounds and derivatives (alone or in combination with DNA damaging agents) for treating lymphomas that are C-circle positive.

Use of PRIMA-1, APR-246, and related compounds and derivatives (alone or in combination with DNA damaging agents) for treating leukemias that are C-circle positive.

Use of PRIMA-1, APR-246, and related compounds and derivatives (alone or in combination with DNA damaging agents) for treating soft-tissue sarcomas that are C-circle positive.

Use of PRIMA-1, APR-246, and related compounds and derivatives (alone or in combination with DNA damaging agents) for treating ovarian adenocarcinomas that are C-circle positive.

Use of PRIMA-1, APR-246, and related compounds and derivative (alone or in combination with DNA damaging agents) for treating leiomyosarcomas that are C-circle positive.

Use of PRIMA-1, APR-246, and related compounds and derivatives (alone or in combination with DNA damaging agents) for treating breast carcinomas that are C-circle positive.

Use of PRIMA-1, APR-246, and related compounds and derivatives (alone or in combination with DNA damaging agents) for treating colorectal adenocarcinomas that are C-circle positive.

Use of PRIMA-1, APR-246, and related compounds and derivatives (alone or in combination with DNA damaging agents) for treating glioblastomas that are C-circle positive.

Use of PRIMA-1, APR-246, and related compounds and derivatives (alone or in combination with DNA damaging agents) for treating pancreatic neuroectodermal tumors (PNET) that are C-circle positive.

Use of PRIMA-1, APR-246, and related compounds and derivatives in combination with agents that deplete glutathionine (such as buthinonine sulfoximine) for treating cancers with the alternate telomere lengthening (ALT) phenotype, regardless of TP53 mutation status or histological type.

Use of the C-circle assay to identify cancers that will be highly sensitive to PRIMA-1, APR-246, and/or related compounds and derivatives (alone or in combination with DNA damaging agents).

Use of the C-circle assay on circulating DNA in plasm a to identify cancers that will be highly sensitive to PRIMA-1, APR-246, and/or related compounds and derivatives (alone or in combination with DNA damaging agents).

Use of PRIMA-1, APR-246, and related compounds and derivatives in combination with agents that deplete glutathionine (such as buthinonine sulfoximine) for treating neuroblastomas that are C-circle positive.

Use of PRIMA-1, APR-246, and related compounds and derivatives in combination with agents that deplete glutathionine (such as buthinonine sulfoximine) for treating osteogenic sarcomas that are C-circle positive.

Use of PRIMA-1, APR-246, and related compounds and derivatives in combination with agents that deplete glutathionine (such as buthinonine sulfoximine) for treating lymphomas that are C-circle positive.

Use of PRIMA-1, APR-246, and related compounds and derivatives in combination with agents that deplete glutathionine (such as buthinonine sulfoximine) for treating lung adenocarcinomas that are C-circle positive.

Use of PRIMA-1, APR-246, and related compounds and derivatives in combination with agents that deplete glutathionine (such as buthinonine sulfoximine) for treating soft-tissue sarcomas that are C-circle positive.

Use of PRIMA-1, APR-246, and related compounds and derivatives in combination with agents that deplete glutathionine (such as buthinonine sulfoximine) for treating ovarian cystadenocarcinomas that are C-circle positive.

Use of PRIMA-1, APR-246, and related compounds and derivatives in combination with agents that deplete glutathionine (such as buthinonine sulfoximine) for treating leiomyosarcomas that are C-circle positive.

Use of PRIMA-1, APR-246, and related compounds and derivatives in combination with agents that deplete glutathionine (such as buthinonine sulfoximine) for treating breast carcinomas that are C-circle positive.

Use of PRIMA-1, APR-246, and related compounds and derivatives in combination with agents that deplete glutathionine (such as buthinonine sulfoximine) for treating colorectal adenocarcinomas that are C-circle positive.

Use of PRIMA-1, APR-246, and related compounds and derivatives in combination with agents that deplete glutathionine (such as buthinonine sulfoximine) for treating glioblastomas that are C-circle positive.

Use of PRIMA-1, APR-246, and related compounds and derivatives in combination with agents that deplete glutathionine (such as buthinonine sulfoximine) for treating pancreatic neuroectodermal tumors that are C-circle positive.

BRIEF DESCRIPTION OF THE DRAWINGS

For a more complete understanding of the present invention and for further objects and advantages thereof, reference may now be had to the following description taken in conjunction with the accompanying drawings in which.

DETAILED DESCRIPTION

Figure 1:
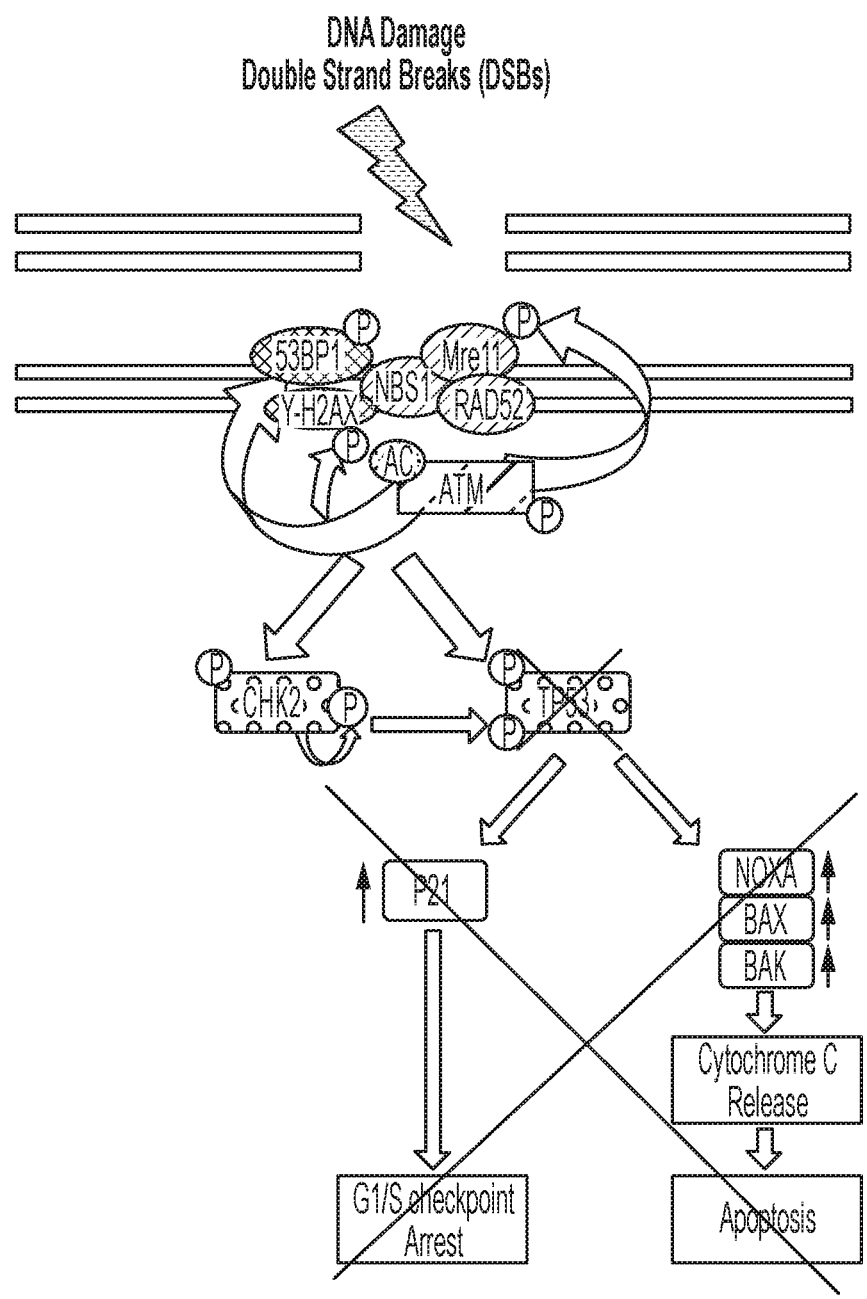
FIG. 1 is an illustration of DNA damage double strand breaks.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

Direct evidence for ALT in NB (and models to enable studying ALT) was provided by screening 40 NB cell lines for TERT expression (defined by TERT mRNA level) and c-circle content. Two NB cell lines were identified with a "classical" ALT phenotype (low TERT, high telomere content, c-circle positive), one of which had an ATRX mutation. It was observed that two NB cell lines had low TERT and very high telomere content, but were c-circle negative, which suggested the possibility of a second ALT mechanism in NB. Further studies of NB cell lines with low telomerase that were c-circle negative confirmed that there exists a group of NB cell lines distinct from ALT that was termed the ever-shortening telomere (EST) phenotype. A recent screening of 130 NB cell lines and PDXs identified additional instances of both ALT and EST NB cell lines and PDXs. Interestingly, the SK-N-FI ALT NB cell line and COG-N-589x ALT NB PDX were ATRX-wt and expressed ATRX protein indicating that ATRX mutations are not essential for ALT. Thus, the ALT phenotype is a distinct molecular phenotype, not merely a manifestation of ATRX mutation, that is best identified using the C-circle assay.

There are approximately 200 high-risk NB patients in the USA per year, and with 20% being ALT, there are on average 40 patients per year who would benefit from a therapy targeting ALT. However, there have been a paucity of ALT patient-derived models established from cancers and due to the high-frequency of ALT (20%) in neuroblastoma and the large number of neuroblastoma cell lines and PDXs, we have established the largest panel of patient-derived cell lines and PDXs with ALT as our neuroblastoma panel. The paucity of patient-derived ALT+ cell lines and PDXs in other cancers in part likely reflects what we have observed in NB, namely that ALT cancers are more difficult to grow as cell lines or as PDXs.

Other cancers have been reported to commonly manifest ALT, such as pancreatic primitive neuroendocrine tumors, glioblastoma multiforme, and osteosarcoma, all provide highly viable commercial potential for therapies targeting ALT. In screening for ALT in our cell line and PDX panel, we have also identified lymphomas, rhabdomyosarcomas, colorectal, breast, leiomyosarcoma, lung, and ovarian cell lines and PDXs that are of the ALT phenotype.

PRIMA-1

One of the most common, if not the most common, genes mutated in human cancers is the TP53 gene, which codes for a transcription factor (p53) that is key in the response of cells to genotoxic stress. Genotoxic stress, such as DNA damaging radiation or drugs, induces p53 expression and activity and leads to cell cycle arrest and repair of damaged DNA. Rapidly proliferating cells, especially those driven to progress in the cell cycle (such as cancer cells), often instead are pushed into cell death by p53 inducing apoptosis rather than an arrest and repair of the cell. Loss of p53 function by cancer cells (often due to inactivating mutations of TP53) results in increased resistance to DNA damaging chemotherapy and also to radiation, both of the latter are considered to have p53-dependent cytotoxicity. Some drugs can kill cancer cells by mechanisms that do not require p53 function and are p53-independent, but often cancer cells are more sensitive to drugs, including p53-independent drugs, if they have functional p53.

Many p53-inactivating mutations act by causing a conformational change of p53 that renders the molecule incapable of binding to DNA consensus sequences that recognize p53 and promote transcription of genes that cause growth arrest (such as p21) or apoptosis (such as bax). Using a screen of a large chemical library to seek compounds that could bind to mutated p53 and restore p53 function, investigators identified bis(hydroxymethyl_-3-quinuclidinone, which was named PRIMA-1 for its activity to restore p53 function and induce massive apoptosis. The methylated form of PRIMA-1, APR-246, was developed for clinical trials. APR-246 had preclinical activity in both solid tumors and hematological malignancies, and was taken into a phase I trial in hematological malignancies and hormone-refractory prostate cancer. In the first-in-human phase I clinical trial the most common adverse events were dizziness, headache, confusion, and other neurological complications; bone marrow toxicity was not observed. At the maximally tolerated dose (60 μg/m2) a C-max of ~60 mg/m$^2$ was obtained, and plasma levels >10 μg/ml were seen out to ~12 hours. The drug sponsors clearly sought to further study the drug in a population with a very high incidence of TP53 inactivating mutations (given the preclinical studies indicating that the drug is most active in that setting) and thus have undertaken a phase II clinical trial in ovarian cancer (where a majority of the patients have tumors with TP53 mutations). While it is possible that sufficient activity of APR-246 would be observed in that phase II trial to enable an FDA registration for APR-246, or to inform a subsequent randomized clinical trial, it is also possible (given data from clinical and non-clinical studies it is actually likely) that only a subset of TP53-mutated cancers will respond to APR-246. Also, there are no compelling published preclinical studies that would suggest ovarian cancer is a particularly responsive cancer for APR-246. For these reasons, identifying a cancer type, or best a molecular phenotype of cancer, for which a biomarker exists to select patients for entry onto a clinical trial would be of particular interest.

Clinical development of APR-246 could be greatly accelerated, with a substantial reduction in costs and time to market, if a biomarker were to be identified that could identify patients with tumors likely to respond to APR-246. Such a biomarker could be used to identify patients for a single-arm phase II registration trial, and registration could be based on observing a significant number of patients with durable responses, with the FDA granting registration for APR-246 to treat all cancers that possess such a biomarker. The recent approval of Keytruda® for treating any patient with microsatellite instability (MSI) by the FDA serves as an excellent model for such an approach. In the case of Keytruda®, the FDA granted a registered indication to treat any cancer with MSI, and data were not required for every possible cancer type. Approval was granted to treat pediatric cancers with no pediatric data. Thus, a biomarker of a molecular phenotype with a high response rate to APR-246 would have significant diagnostic potential. Even more important would be a biomarker that could not only be assessed with patient tumor biopsies but also detected in plasma.

C-Circles as a Biomarker for ALT Cancers

The C-circle assay has been considered as specific for the ALT pathway. We studied our panel of adult and pediatric patient-derived cell lines and PDXs for TERT expression and C-circles, together with other hallmarks of ALT (long heterogenous telomeres, presence of APB's and lack of telomerase activity). We recently defined another subset of TERT-low neuroblastomas which are not C-circle positive, further emphasizing the value of the C-circle assay as a biomarker of a distinct biological (and targetable) subset of cancers (manuscript in preparation). We have also demonstrated that the C-circle assay can identify a large subset of other cancers that are ALT+ including pancreatic neuroectodermal tumor patient primary tumors (see Table 1).

We have determined that the C-circle assay (specific for ALT cancers) identifies cancers that are especially responsive to PRIMA-1. While PRIMA-1 and APR-246 are being developed to treat TP53-mutated caners, only a subset of the latter respond to the drug as shown in preclinical studies and in the early phase I clinical trials. Studying neuroblastoma cell lines we found that only a subset of neuroblastomas respond exceptionally well to PRIMA-1 and that subset is the ALT cancers. Activity of PRIMA-1 is significantly higher in ALT neuroblastoma than it is in non-ALT neuroblastoma, even if the non-ALT cancers have TP53-inactiving mutations. We have begun examining activity of PRIMA-1 in cell lines from other ALT cancers and we have observed data that are consistent with the C-circle assay being a specific marker that can identify cancers highly responsive to PRIMA-1 or APR-246. Moreover, we have preliminary data that suggest that we can detect the presence of an ALT cancer in a patient by assaying C-circles in plasma. Thus, we have likely identified an ideal biomarker for PRIMA-1, which will be of great commercial potential as it would enable carrying out clinical trials enriched (with a robust biomarker) for likely responders, and would enable seeking a cross-disease (and cross ages) indication for treating a molecular phenotype found in several cancer histologies.

TABLE 1

C-Circle Assay Screening Results

| | Previously Reported | Our Work | | | | | |
|---|---|---|---|---|---|---|---|
| Cancer Type | Frequency of ALT in Patient Tumors | Number of Cell Lines/PDXs Screened | Number ALT+ | % ALT+ | Number of Patient Tumors Screened | Number ALT+ | % ALT+ |
| Neuroblastoma | 20% | 175 | 5 | 3% | 110 | 25 | 23% |
| Osteosarcoma | 85% | 7 | 4 | 57% | In progress | | |
| Gliobastoma | 28% | 4 | 0 | 0% | In progress | | |
| Pancreatic | 53% | 0 | 0 | 0% | 21 | 9 | 43% |
| Neuroectodermal Rhabdomyosarcoma | Unreported | 12 | 3 | 25% | 40 | 6 | 15% |
| Lymphoma | Unreported | 20 | 3 | 15% | In progress | | |
| Leiomyosarcoma | 59% | 2 | 1 | 50% | In progress | | |
| Colorectal | 6% | 16 | 3 | 19% | In progress | | |
| Breast | 2% | 10 | 1 | 10% | In progress | | |
| Lung | 1% | 24 | 1 | 4% | In progress | | |
| Ovarian | 1% | 19 | 1 | 5% | In progress | | |

FIG. 1 is an illustration of DNA damage double strand breaks. ALT cancers activate ATM kinase causing a constitutive DNA-damage response phenotype. While the mechanism of ALT is not completely understood, it has been linked by other investigators to both the ATR and ATM pathways which are integral to DNA damage response. Using our extensive panel of patient-derived ALT models we have shown that (likely due to dysfunctional telomeres in ALT cancer cells) ATM kinase is activated continuously in ALT cancers. Cancer cells survive the continual signaling that DNA damage is occurring by having an inactivated p53 pathway, which is a primary mechanism for a cytotoxic response of cells to DNA damage.

Constitutive Activation of ATM in ALT+ Cells

Figure 2A:
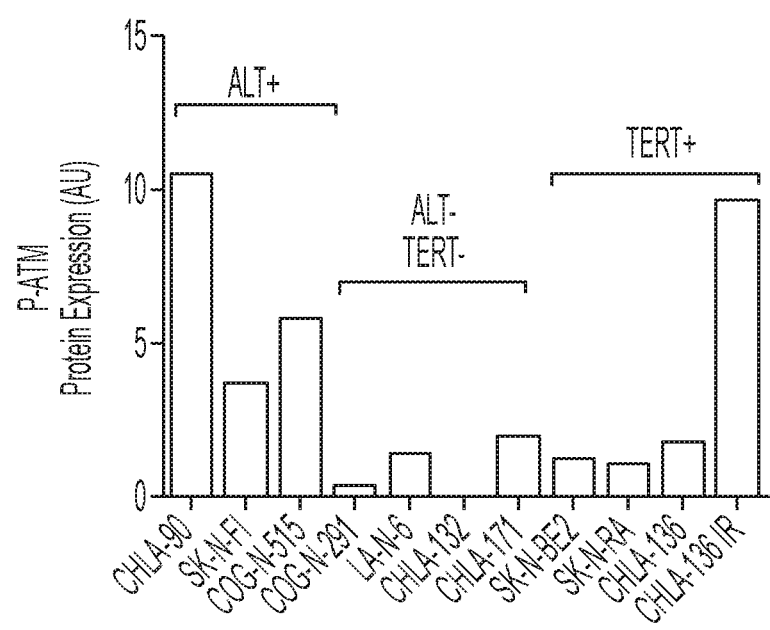
FIGS. 2A and 2B are graphs illustrating the amount of P-ATM and P-CHK2 present in cells that are ALT+ vs TERT+ vs ALT−, TERT−.
Figure 2B:
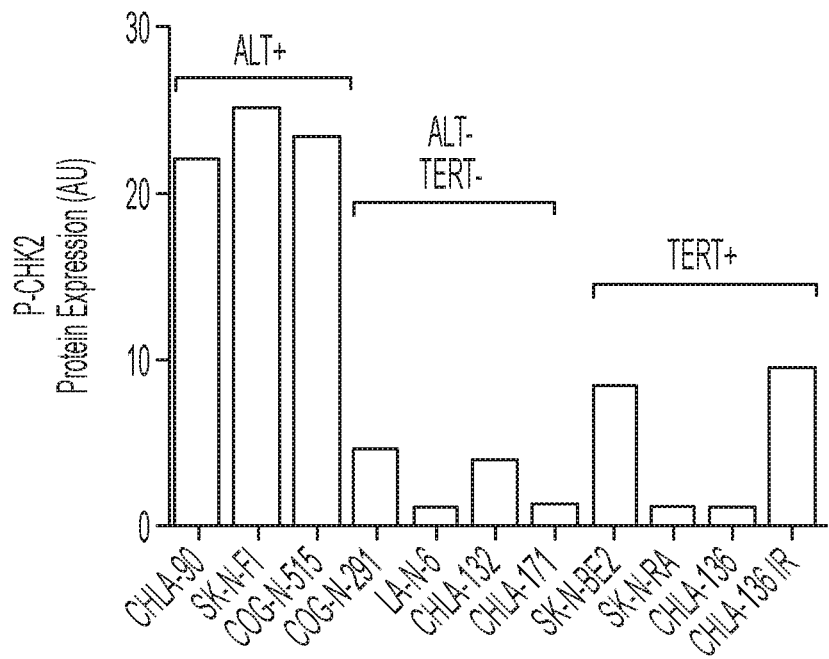

ATM was present in all of the cell lines above including those which have telomerase (TA+) or lack telomerase but are ALT (C-circle+). FIG. 2A illustrates that phosphorylated (activated) ATM was observed in ALT+ but not TA+ cell lines. FIG. 2B illustrates that the ATM downstream target Chk2 was heavily phosphorylated in ALT cells vs non-ALT cell lines. P-ATM immunostaining was observed in ALT+ cell lines but not in non-ALT, TA+ or the TERT-low ever shortening of telomeres (EST) phenotype such as COG-N-291, which is both telomerase and C-circle negative.

ALT and Non-ALT Cell Lines have Different ATM Responses to DNA Damage

P-ATM was induced in ALT and non-ALT TERT+ cells using radiation. In the ALT+ cell line CHLA-90, P-ATM was highly expressed even without exposure to a DNA damaging agent. After treatment with radiation, the cells showed a slight increase in P-ATM before returning to their initial levels after 24 hours. The non-ALT TERT+ cell line SK-N-BE(2) had a low basal P-ATM and radiation caused a high induction of P-ATM that returned to basal low levels after 24 hours. These data suggest that ALT cells manifest a molecular phenotype that resembles treatment with a DNA damaging agent and thus may be especially susceptible to reactivation of the p53 pathway, which is commonly inactivated in ALT cancers.

Figure 3:
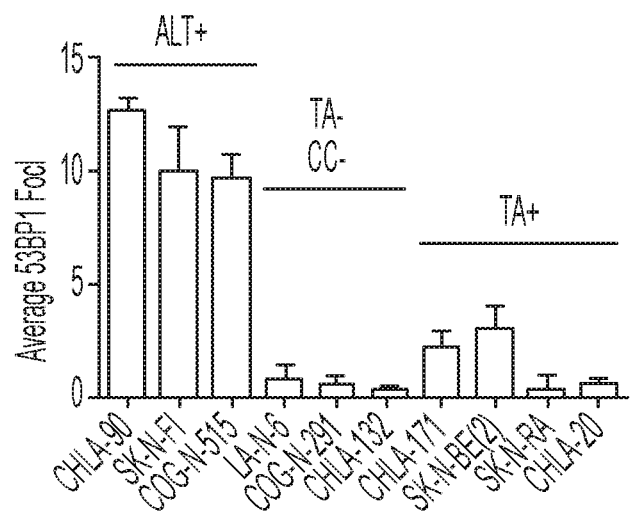
FIG. 3 is a graph of average 53BP1 Foci for various cell lines showing high intrinsic DNA damabe (detection of 53BP1) in ALT vs non-ALT cancer cell lines.

Constitutively High 53BP1 is Observed in ALT but Not Non-ALT Neuroblastoma Cell Lines FIG. 3 is a graph of average 53BP1 Foci for various cell lines. 53BP1 is a protein that localizes to sites of DNA damage in cells after ATM is activated. Immunostaining for 53BP1 showed high levels in ALT (C-circle+) cell lines but not in telomerase (TA) negative/C-circle negative lines (i.e. EST lines) or in telomerase+ cell lines.

ALT+ Cancers are Selectively Vulnerable to Reactivation of p53 Function

Figure 4:
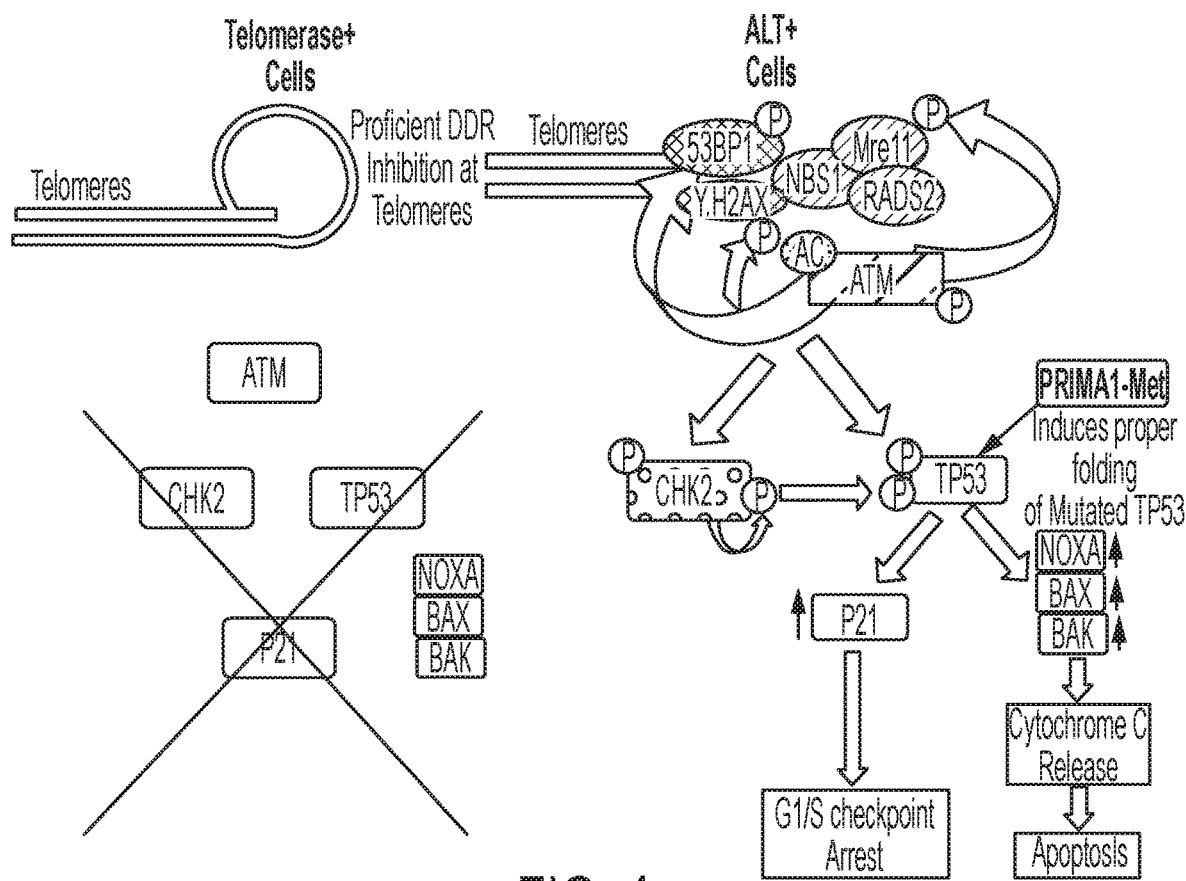
FIG. 4 is an illustration of ALT+ cancers vulnerability of p53 function.

FIG. 4 is an illustration of ALT+ cancers vulnerability of p53 function. Our hypothesis, based on our novel data on ATM in ALT cancers obtained with our novel set of patient-derived ALT models, is that non-ALT cancers (TERT+) will not have a constitutive activation of the DNA damage-sensing pathway and thus require treatment with PRIMA-1MET but that ALT+ cancers having constitutively activated the DNA damage repair pathway will be highly sensitive to PRIMA-1MET as a single agent and especially in combination with other agents. Thus, ALT cancers, identified by the C-circle assay, will be the most sensitive to PRIMA-1MET as a single agent or in drug combinations.

Figure 5A:
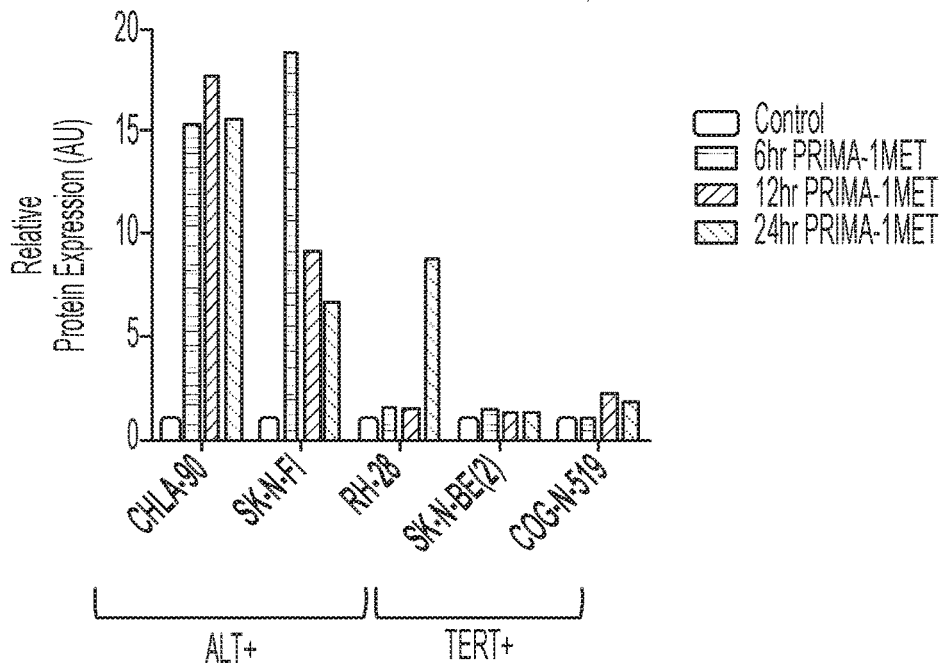
FIGS. 5A and 5B are graphs of the high induction of p21 and NOXA with PRIMA-1MET in ALT+ vs low induction in TERT+ cell lines.
Figure 5B:
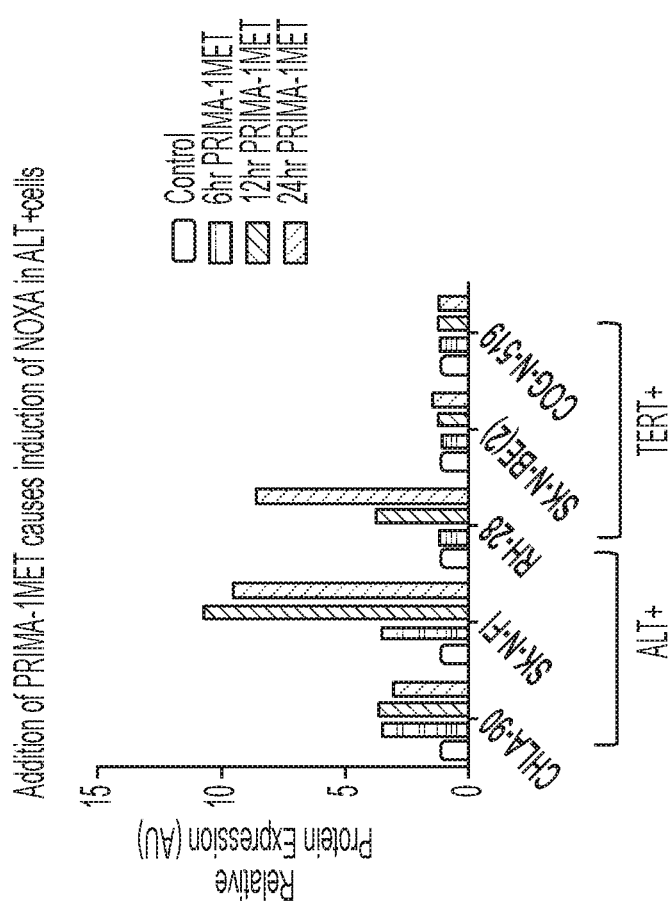

PRIMA-1MET Induces p21 and NOXA in ALT but Not in Non-ALT Neuroblastoma Cell Lines FIGS. 5A and 5B are quantitative representations of immunoblots of apoptotic proteins with three ALT+ cell lines and two TERT+ lines. All cell lines were treated with 20 μM of PRIMA-1MET for 6, 12 and 24 hours. All cell lines were known to have TP53-inactivating mutations. The ALT+ lines demonstrated a substantial increase in p21 expression when exposed to PRIMA-1MET followed by NOXA expression during longer treatment. The non-ALT cell lines show very little increase in expression of p21 or NOXA. We hypothesize this is due to the constitutive activation of ATM in ALT positive cell lines, which will trigger senescence and apoptosis once PRIMA-1MET refolds mutant TP53.

Expression of Functional p53 Induces p21 in ALT but Not in Non-ALT Neuroblastoma Cell Lines Functional p53 was cloned and placed into the TERT+ cell line CHLA-119 and the ALT+ lines CHLA-90 and SK-N-FI in a vector with a tetracycline inducible promotor. Doxycycline (DOX) was added to induce p53. All cell lines in this experiment have non-functional p53. When functional p53 was induced with DOX, p21 expression was induced in the ALT+ cell lines (CHLA-90 and SK-N-FI) while the TERT+ line CHLA-119 did not show induction of p21. These data suggest that the high amount of P-ATM constitutively present in ALT+ cells acts the same as a DNA damaging agent to induce p21. These data again point toward the mechanism by which ALT cells will be hypersensitive to PRIMA-1 and similar compounds.

Figure 6:
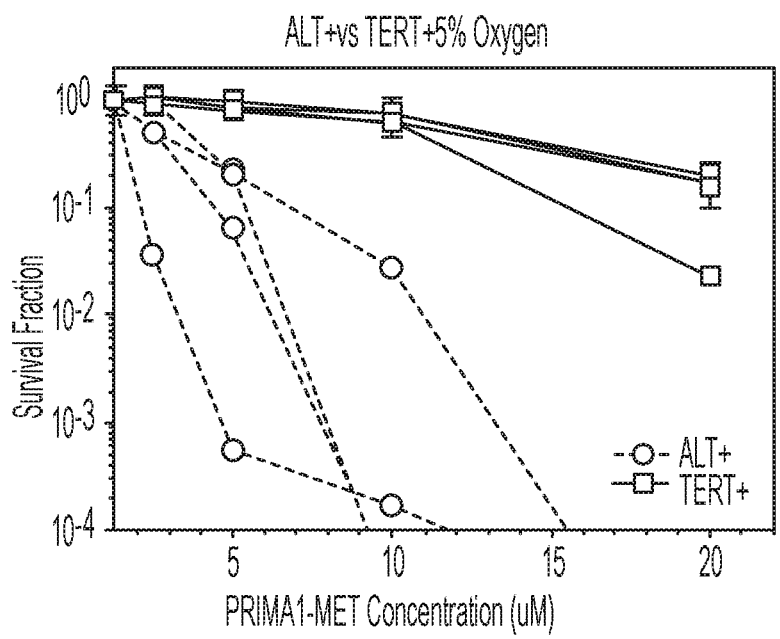
FIG. 6 is a graph of survival fraction versus PRIMA-1MET concentration for NB cultured in 5% $O_2$ demonstrating higher sensitivity of ALTNB cell lines compared to TERT+ (non-ALT) NB cell lines.

ALT+ Neuroblastoma Cell Lines are Highly Sensitive to PRIMA-1MET Relative to Non-ALT (TERT+) Lines FIG. 6 is a graph of survival fraction versus PRIMA-1MET concentration and illustrates high cytotoxicity of PRIMA-1MET in ALT+ versus TERT+ (ALT negative) NB cell lines. FIG. 6 illustrates NB 5% $O_2$. PRIMA-1MET dose response curves were analyzed using the DIMSCAN cytotoxicity assay system in 4 ALT+ neuroblastoma cell lines compared to 3 non-ALT, but TP53-mut cell lines. The ALT cell lines were significantly more sensitive to PRIMA-1MET than non-ALT cell lines.

Hypoxia Enhances PRIMA-1MET Cytotoxicity for ALT Neuroblastoma Cell Lines

Figure 7A:
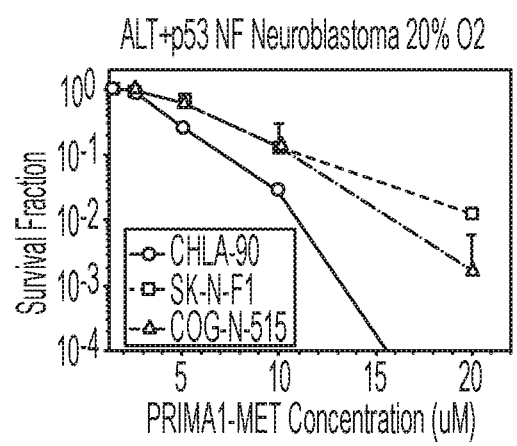
FIGS. 7A and 7B are graphs of survival fraction versus PRIMA-1MET concentration for ALT+ p53 non-functional NB in 20% $O_2$, and ALT+ p53 non-functoinal NB in 5% O, demonstrating the increased activity against of PRIMA1MET against ALT NB cell lines in hypoxia.
Figure 7B:
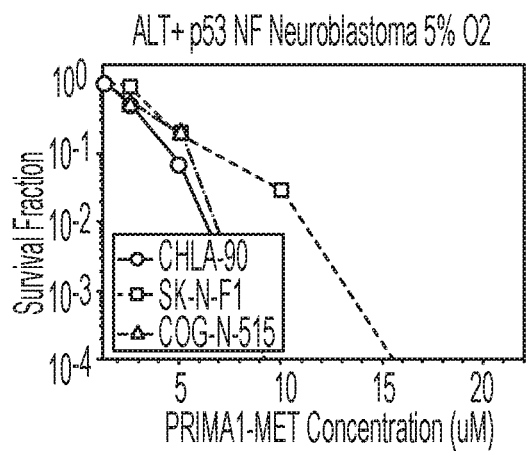

FIGS. 7A and 7B are graphs of survival fraction versus PRIMA-1MET concentration and illustrate cytotoxicity of PRIMA-1MET in ALT+ NB cell lines as enhanced by hypoxia. PRIMA-1MET cytotoxicity was assessed for 3 ALT neuroblastoma cell lines in ambient air culture conditions (20% $O_2$) compared with bone marrow level hypoxia (5% $O_2$). PRIMA-1MET shows even great cytotoxicity for ALT cell lines in hypoxia.

ALT Rhabdomyosarcoma Cell Lines are Highly Sensitive to PRIMA-1MET

Figure 8A:
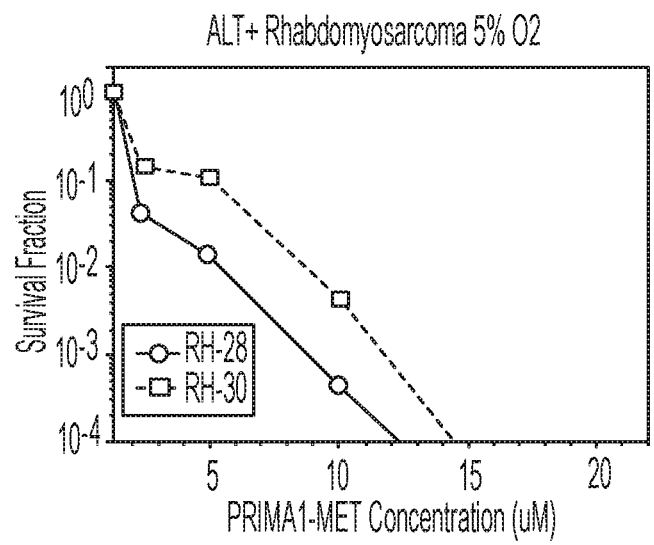
FIGS. 8A and 8B are graphs of survival fraction versus PRIMA-1MET concentration for ALT+ Rhabdomyosarcoma 5% $O_2$ and TERT+ Rhabdomyosarcoma 5% $O_2$.
Figure 8B:
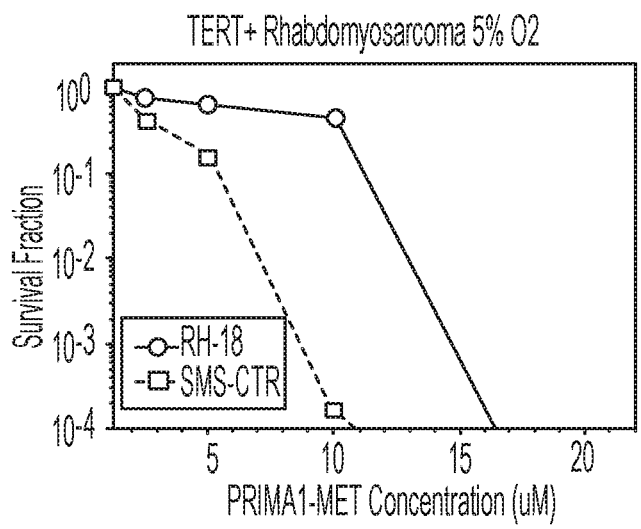

FIGS. 8A and 8B are graphs of survival fraction versus PRIMA-1MET concentration and illustrate Cytotoxicity of PRIMA-1MET in ALT vs TERT+ Rhabdomyosarcoma. FIG. 8A illustrates ALT+ rhabdomyosarcoma grown in 5% $O_2$ and FIG. 8B illustrates TERT+ rhabdomyosarcoma grown in 5% $O_2$. Cytotoxicity of PRIMA-1MET was assessed for ALT and non-ALT (TERT+) rhabdomyosarcoma cell lines using DIMSCAN. ALT lines were more sensitive to PRIMA-1MET compared to non-ALT lines.

ALT Lymphomas are More Sensitive to PRIMA-1MET than are Non-ALT Lymphomas

Figure 9A:
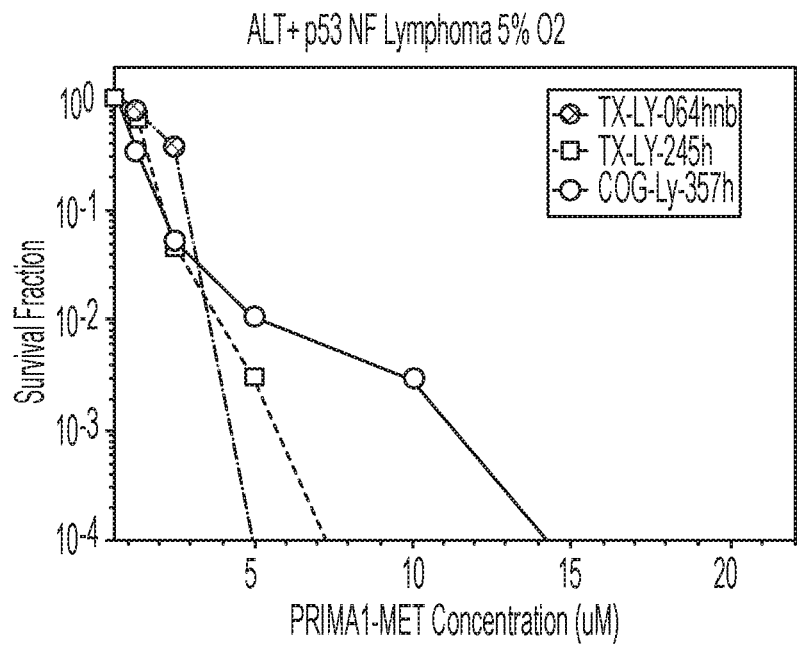
FIGS. 9A and 9B are graphs of survival fraction versus PRIMA-1MET concentration for ALT+ p53 NF lymphoma 5% $O_2$ and TERT+ p53 NF lymphoma 5% $O_2$.
Figure 9B:
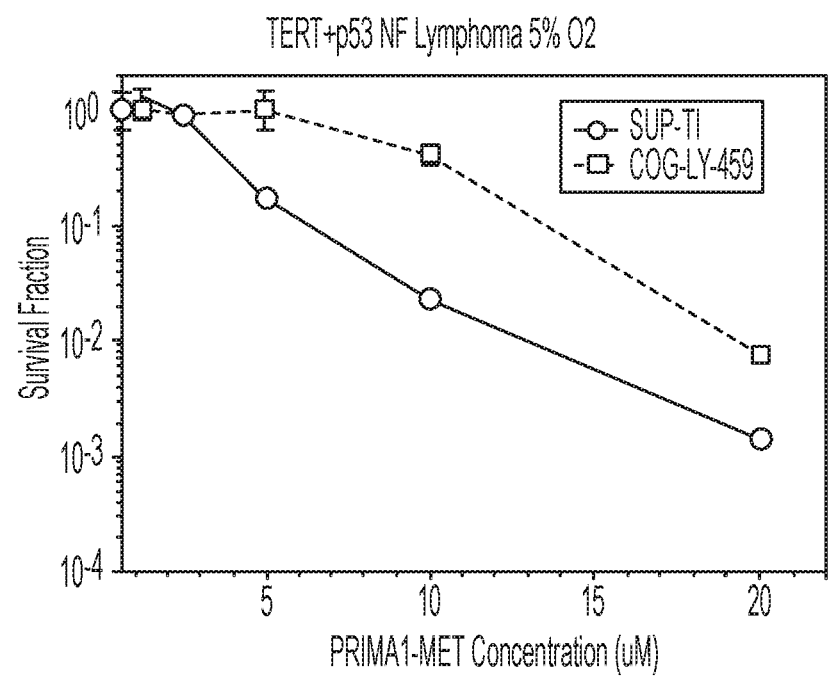

FIGS. 9A and 9B are graphs of survival fraction versus PRIMA-1MET concentration for ALT+ p53 non-functoinal lymphoma 5% $O_2$ and TERT+ p53 non-functional lymphoma 5% $O_2$, respectively. DIMSCAN dose response curves for ALT large B-cell lymphoma cell lines (TX-LY-064hnb and TX-LY-245h) and ALT Pre-T lymphoblastic lymphoma cell line COG-LY-357h were more sensitive than the TERT+ lines SUP-TI and COG-LY-459. All lines had some form of p53 dysfunction.

Figure 10:
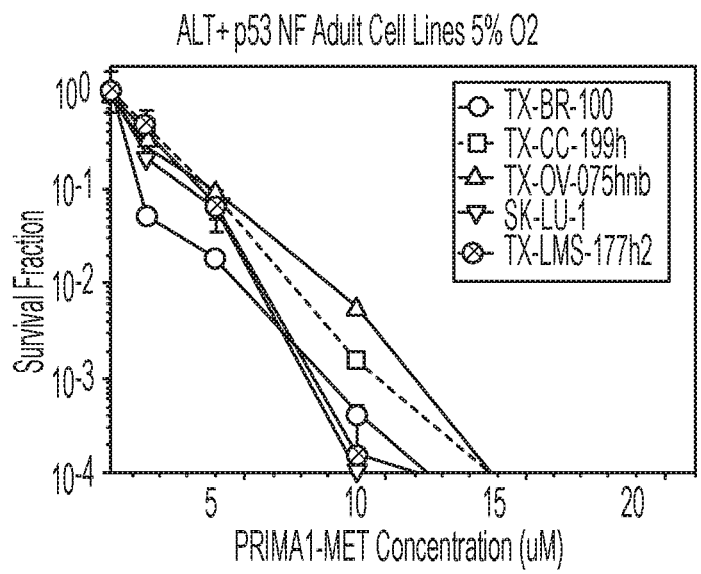
FIG. 10 is a graph of survival fraction versus PRIMA-1MET concentration for ALT+ adult cell lines showing the high activity of PRIMA1MET against ALT breast cancer, colorectal cancer, ovarian cancer, lung cancer, and leiomyosarcoma cell lines.

FIG. 10 is a graph of survival fraction versus PRIMA-1MET concentration for ALT+ p53 non-functional adult cell lines 5% $O_2$. All lines had some form of p53 dysfunction.

ALT Lymphoid Leukemias and Lymphomas are More Sensitive to PRIMA-1MET than are Non-ALT Leukemias and Lymphomas FIGS. 7A and 7B are graphs of survival fraction versus PRIMA-1MET concentration and illustrate cytotoxicity of PRIMA-1MET in ALT+ versus TERT+ lymphoid leukemia and lymphomas. FIG. 7A illustrates ALT+ Leukemia, Lymphoma 5% $O_2$ and FIG. 7B illustrates TERT+ leukemia, lymphoma 5% $O_2$. DIMSCAN dose response curves for ALT acute lymphoblastic leukemia (COG-LL229) and an ALT lymphoma (COG-LY-360) compared to non-ALT leukemia and lymphoma cell lines Summary of PRIMA-1MET Cytotoxicity ALT vs Non-ALT Cell Lines FIGS. 8A-8D are graphs of PRIMA-1MET cytotoxicity of ALT vs non-ALT cell lines and illustrate PRIMA-1MET IC50/IC90 for all tested cancers. FIG. 8A illustrates IC50 20% $O_2$, FIG. 8B illustrates IC90 20% $O_2$, FIG. 8C illustrates IC50 5% $O_2$, and FIG. 8D illustrates IC90 5% $O_2$. Cytotoxicity data on all ALT cell lines from various histologies were compared with non-ALT cell lines of the same histologies, presented as inhibitory+cytotoxic concentrations for 50% (IC50) and 90% (IC90) of the cells. ALT cell lines were significantly more sensitive to PRIMA-1MET than are non-ALT cell lines, and the differences were greater in bone marrow level hypoxia.

PRIMA-1MET+BSO in Non-ALT (TERT+) Neuroblastoma Cell Lines

FIG. 10 is a graph of survival fraction versus PRIMA-1MET concentration for CHLA-172 and illustrates PRIMA-MET with BSO in TERT+ NB. Concentrations of PRIMA-1MET that when combined with BSO achieved multilog cell kills in ALT neuroblastoma cell lines caused minimal cytotoxicity for non-ALT (TERT+) neuroblastoma cell line.

Summary of PRIMA-1MET Cytotoxicity ALT vs Non-ALT Cell Lines

Figure 11A:
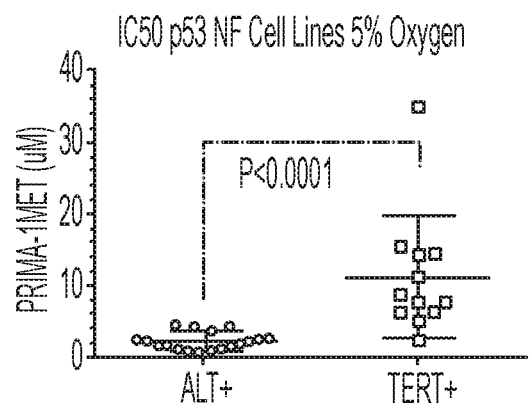
FIGS. 11A and 11B are graphs showing cytotoxicity of ALT and non-ALT cell lines for IC50 and IC90 (concentrations inhibitory/cytotoxic for 50% or 90% of cells)
Figure 11B:
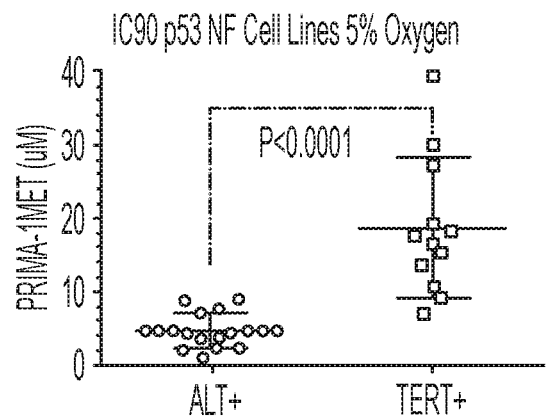

FIGS. 11A and 11B are graphs showing cytotoxicity of ALT and non-ALT cell lines for IC50 and IC90. Cytotoxicity data on all ALT cell lines from various histologies compared with non-ALT cell lines of the same histologies. The data is presented as inhibitory+cytotoxic concentrations for 50% (IC50) and 90% (IC90) of the cells. ALT cell lines are significantly more sensitive to PRIMA-1MET than are non-ALT cell lines.

Figure 12A:
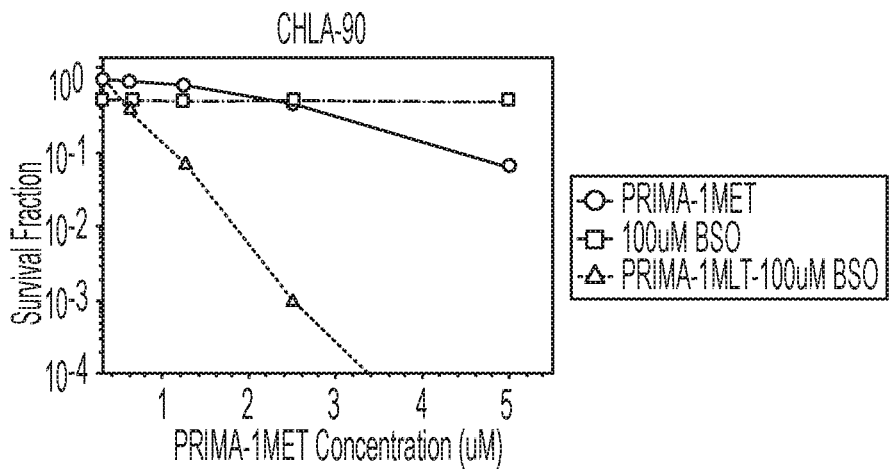
FIGS. 12A, 12B and 12C are graphs of survival fraction versus PRIMA-1MET and BSO concentrations for ALT+ neuroblastoma cell lines CHLA-90, SK-N-FI, and COG-N-512.
Figure 12B:
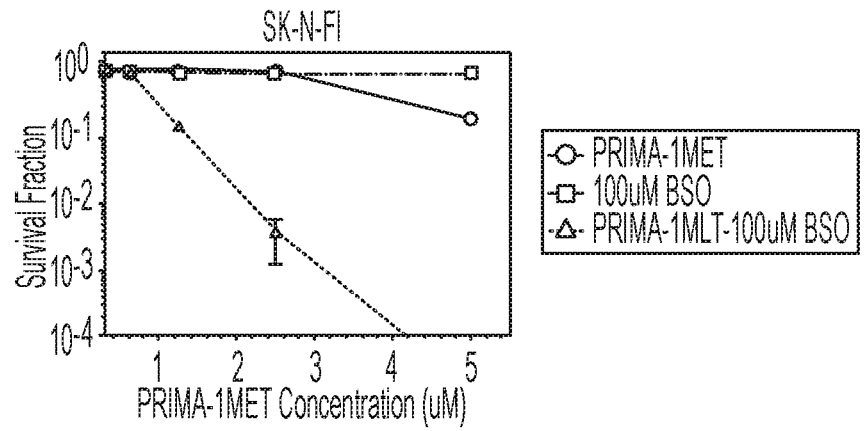
Figure 12C:
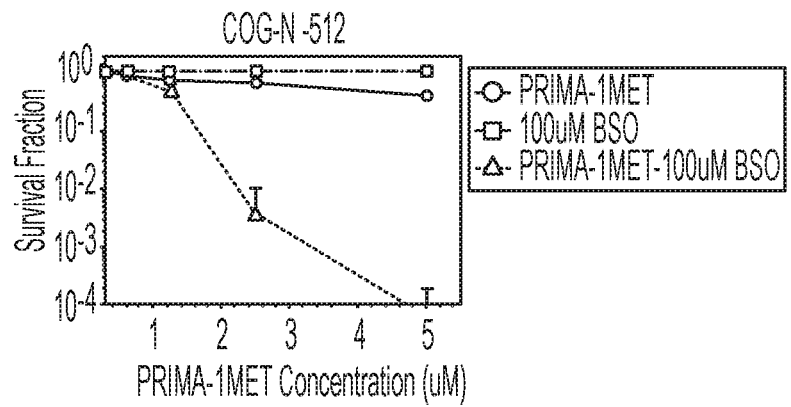

Depletion of GSH with BSO Significantly Enhanced PRIMA-1MET Cytotoxicity for ALT Neuroblastoma Cell Lines FIGS. 12A-12C are graphs of survival fraction versus PRIMA-1MET concentration and illustrate PRIMA-1MET in ALT+ NB. FIG. 12A illustrates CHLA-90, FIG. 12B illustrates SK-N-FI, and FIG. 12C illustrates COG-N-512. Cytotoxicity of PRIMA-1MET for ALT neuroblastoma was significantly enhanced by depleting GSH with clinically-achievable levels of BSO. Note that the concentration range used for PRIMA-1MET in these experiments was substantially lower than used as a single agent, as the cytotoxicity of PRIMA-1MET+BSO is striking at very low PRIMA-1MET concentrations.

PRIMA-1MET+BSO was Highly Active against ALT Osteogenic Sarcoma Cell Lines

Figure 13A:
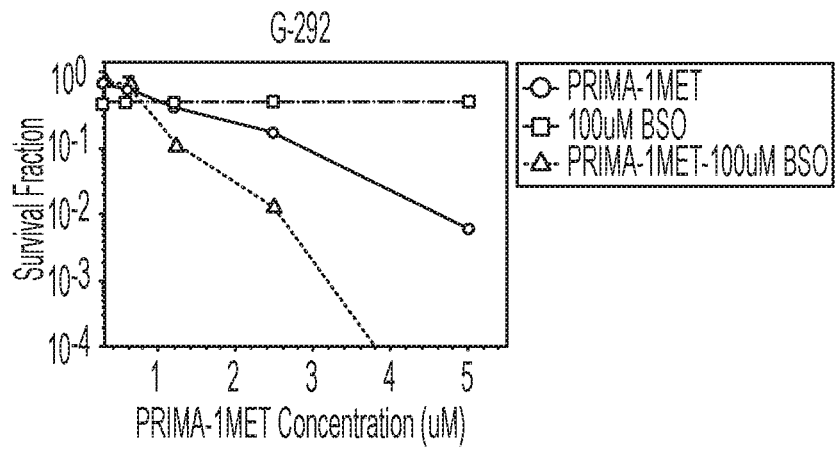
FIGS. 13A and 13B are graphs of survival fraction versus PRIMA-1MET and BSO concentrations for ALT+ osteosarcoma cell lines G-292 and COG-OS-551h.
Figure 13B:
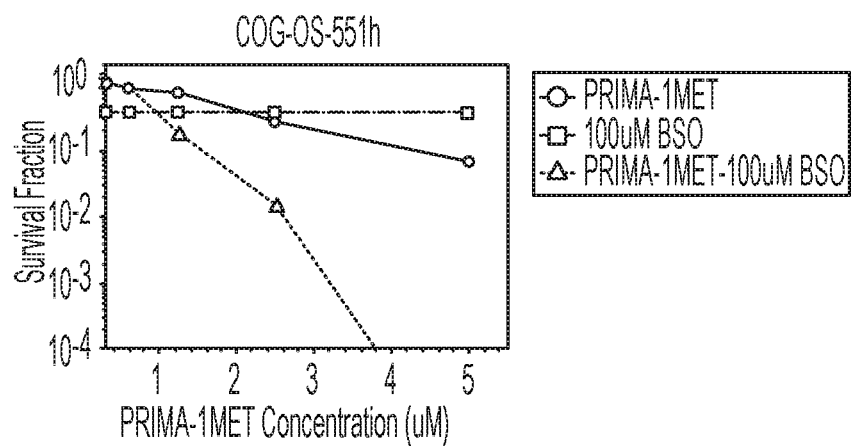

FIGS. 13A and 13B are graphs of survival fraction versus PRIMA-1MET concentration and illustrate PRIMA-1MET+ BSO in ALT+oOsteosarcoma cell line. FIG. 12A illustrates G-292 and FIG. 12B illustrates COG-OS-551.

PRIMA-1MET+BSO was Highly Active against ALT Lymphoma Cell Lines

Figure 14A:
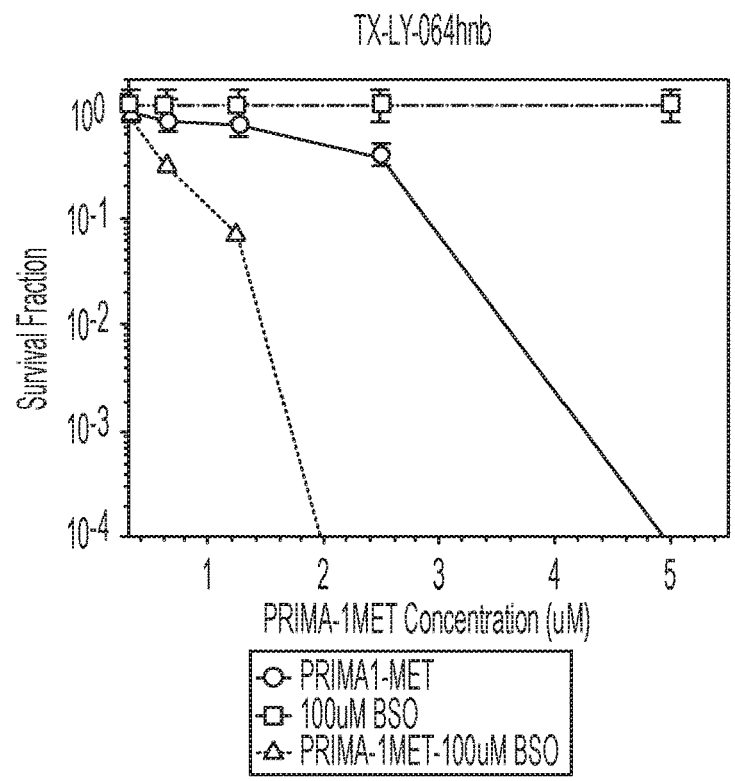
FIGS. 14A, 14B and 14C are graphs of survival fraction versus PRIMA-1MET and BSO concentrations for ALT+ lymphoma cell lines TX-LY-064hnb, TX-LY-245h and COG-LY-357h.
Figure 14B:
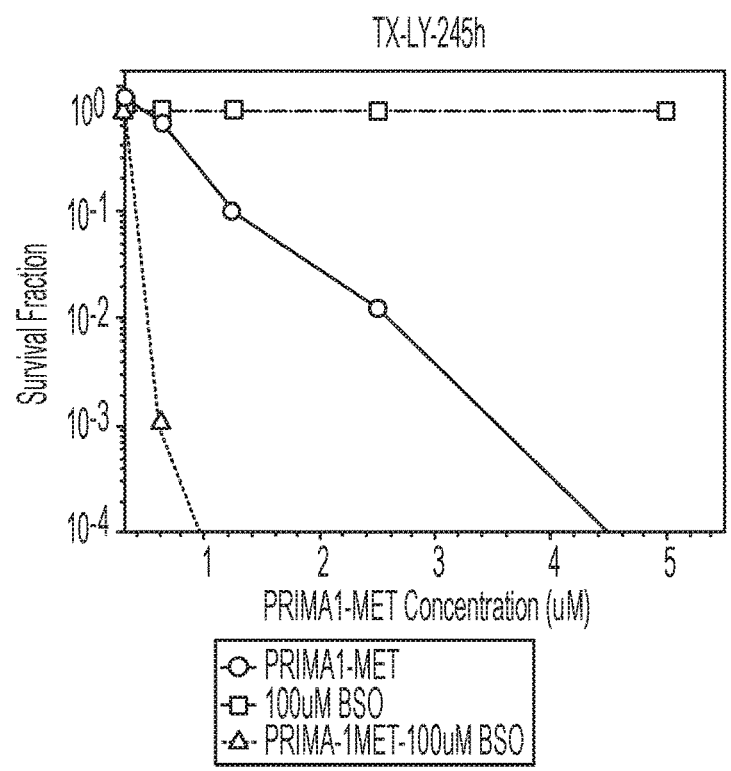
Figure 14C:
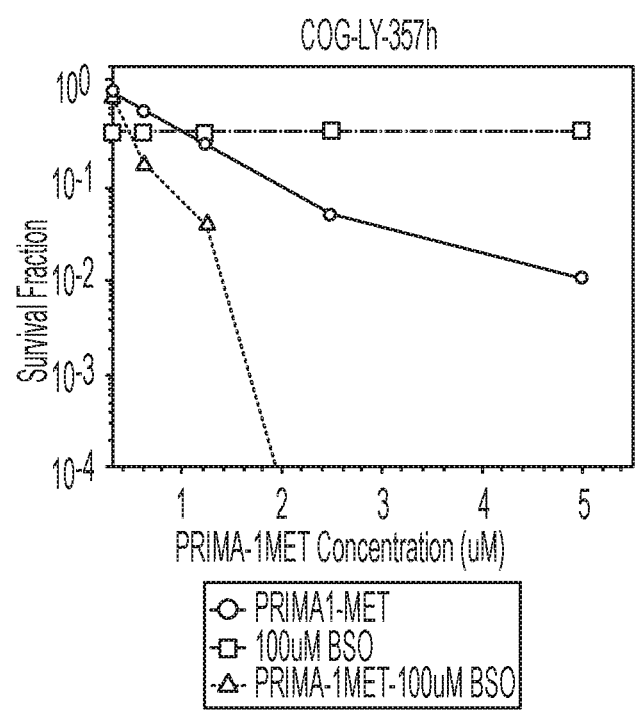

FIGS. 14A-14C are graphs of survival fraction versus PRIMA-1MET concentration and illustrate PRIMA-1MET+ BSO in ALT+ Lymphoma cell lines. FIG. 14A illustrates TX-LY-064hnb, FIG. 14B illustrates TX-LY-245h and FIG. 14C illustrates COG-LY-357h.

PRIMA-1MET+BSO was Highly Active against ALT Triple Negative Breast Cancer Cell Line TX-BR-100

Figure 15:
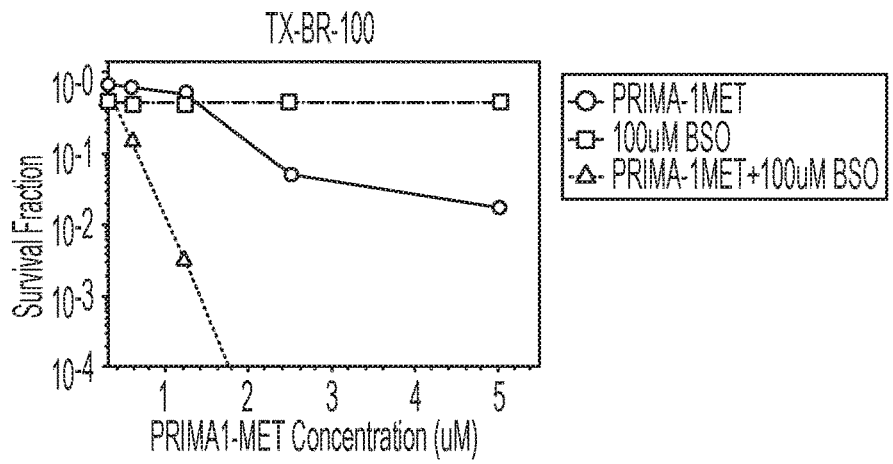
FIG. 15 is a graph of survival fraction versus PRIMA-1MET and BSO concentrations for the ALT+ breast cell line TX-BR-100.

FIG. 15 is a graph of survival fraction versus PRIMA1-MET concentration for TX-BR-100

Figure 16A:
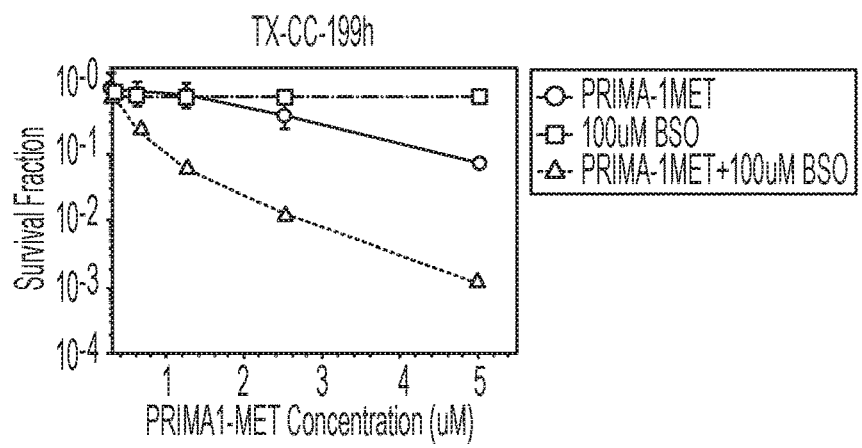
FIGS. 16A and 16B are graphs of survival fraction versus PRIMA-1MET and BSO concentrations for the ALT+ colorectal cell lines TX-CC-199h and TX-CC-208.
Figure 16B:
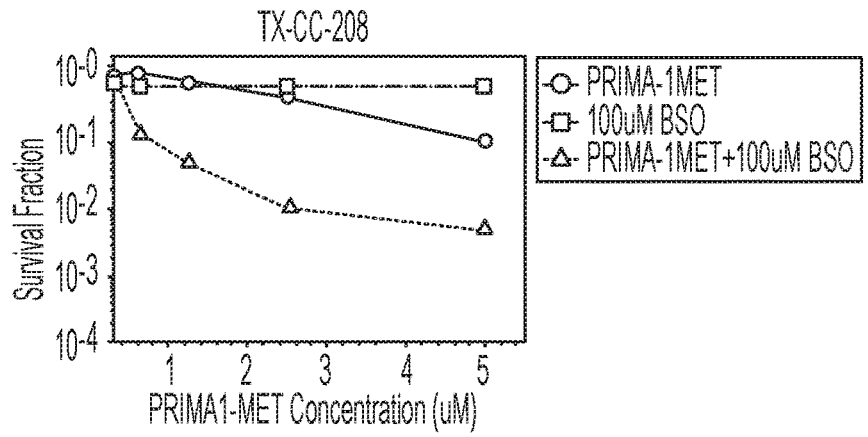

PRIMA-1MET+BSO was Highly Active against ALT Colorectal Adenocarcinoma Cell Lines FIGS. 16A and 16B are graphs of survival fraction versus PRIMA1-MET concentration for TX-CC-199h and TX-CC-208.

PRIMA-1MET+BSO was Highly Active against ALT the Ovarian Cell Line TX-OV-075hnb

Figure 17:
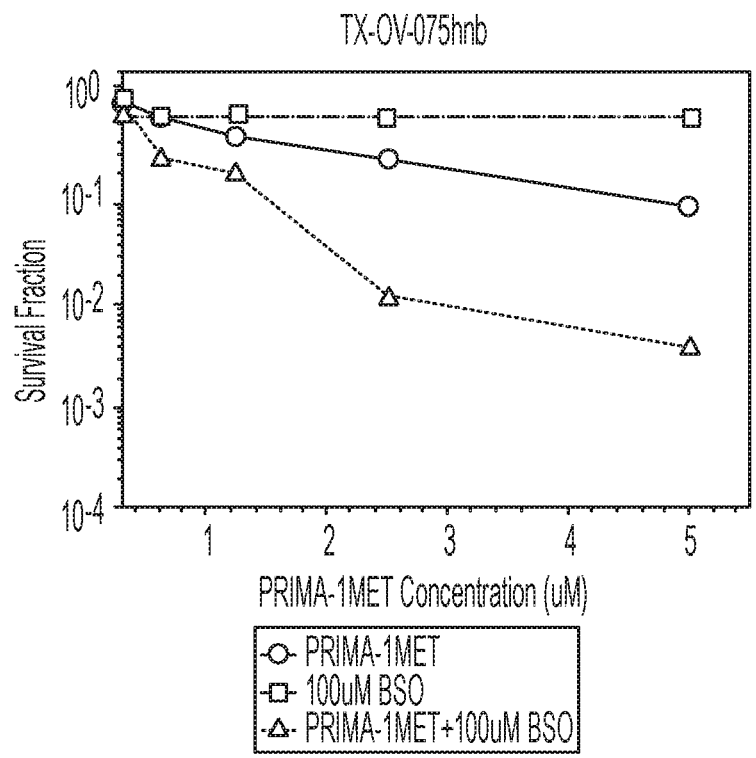
FIG. 17 is a graph of survival fraction versus PRIMA-1MET and BSO concentrations for the ALT+ ovarian cell line TX-OV-075hnb.

FIG. 17 is a graph of survival fraction versus PRIMA1-MET concentration for TX-OV-075hnb.

PRIMA-1MET+BSO was Highly Active against ALT the Leiomyosarcoma Cell Line TX-LMS-177h2

Figure 18:
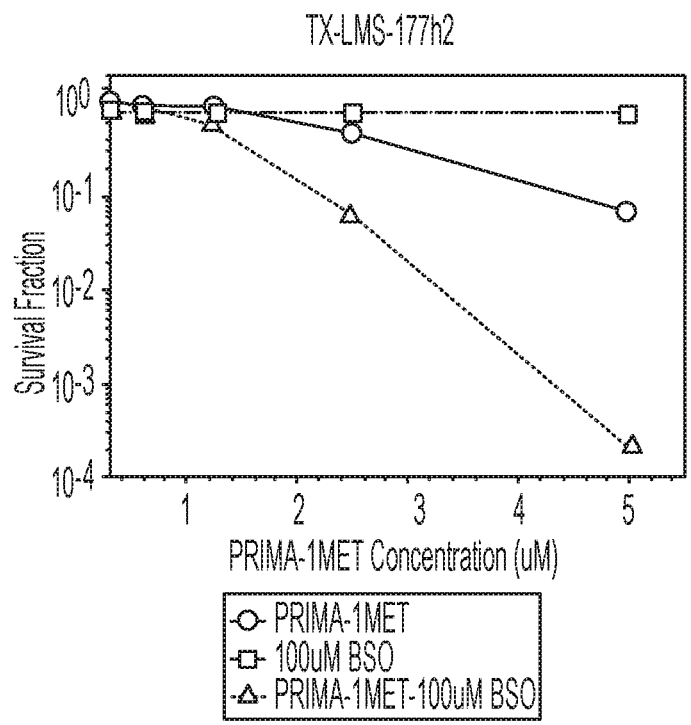
FIG. 18 is a graph of survival fraction versus PRIMA-1MET and BSO concentrations for the ALT+ leiomyosarcoma cell line TX-LMS-177h2.

FIG. 18 is a graph of survival fraction versus PRIMA1-MET concentration for TX-LMS-177h2. PRIMA-1MET+BSO in Non-ALT (TERT+) Cell Lines.

Figure 19A:
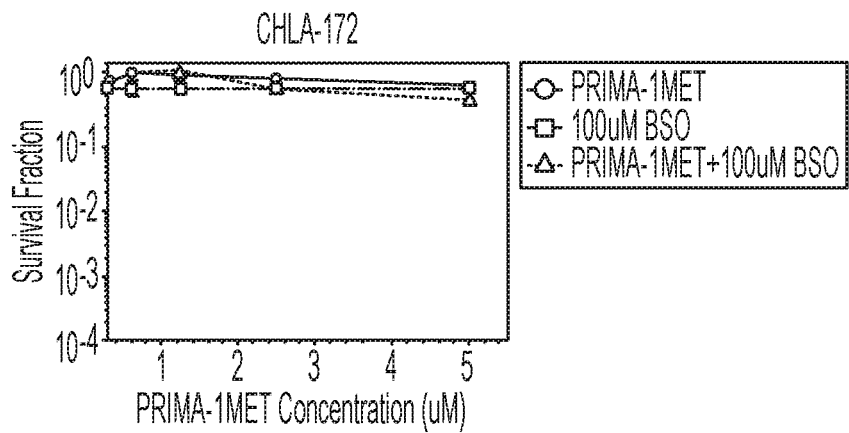
FIGS. 19A, 19B and 19C are graphs of survival fraction versus PRIMA-1MET and BSO concentrations for the TERT+ (non-ALT) cell lines CHLA-172, MG-63, and RH-18.
Figure 19B:
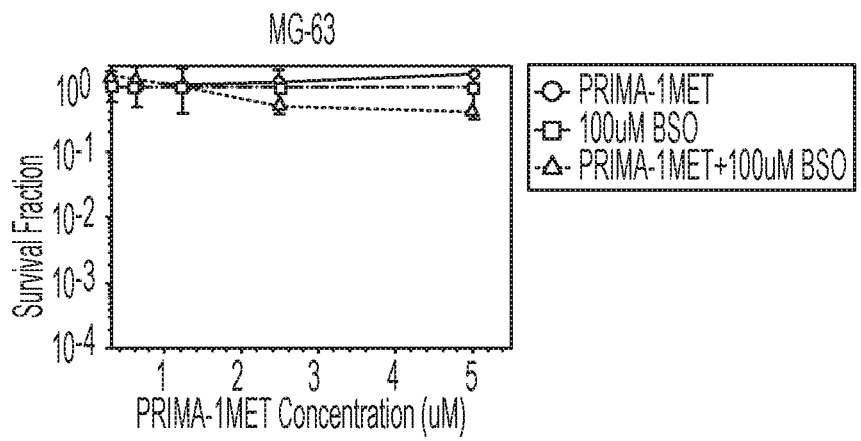
Figure 19C:
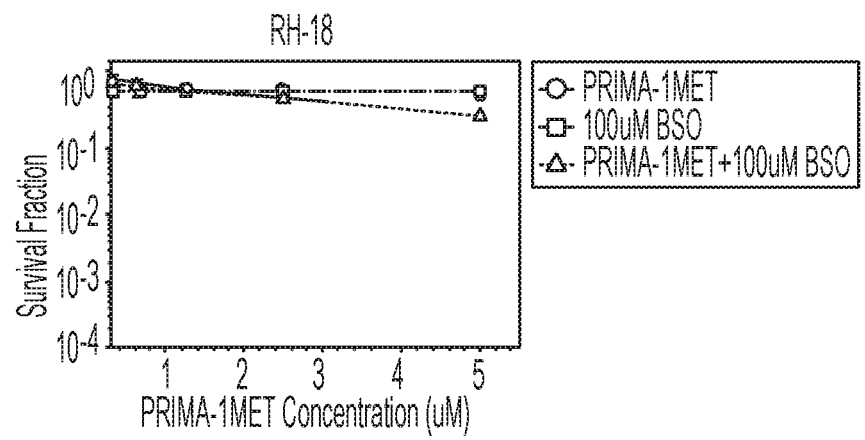

FIGS. 19A-19C are graphs of survival fraction versus PRIMA1-MET concentration for CHLA-172, MG-63, and RH-18. Concentrations of PRIMA-1MET that when combined with BSO achieved multi-log cell kills in ALT cell lines caused minimal cytotoxicity for non-ALT (TERT+) cell lines.

Figure 20A:
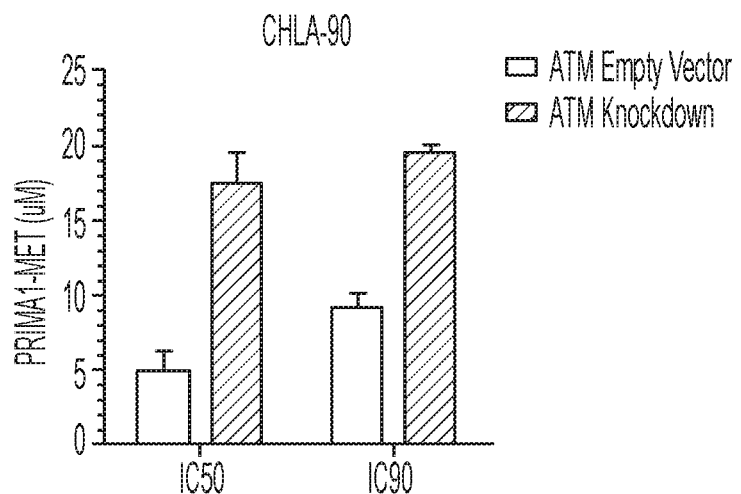
FIGS. 20A and 20B illustrate data for the ALT NB cell line CHLA-90 when knocking down ATM kinase.
Figure 20B:
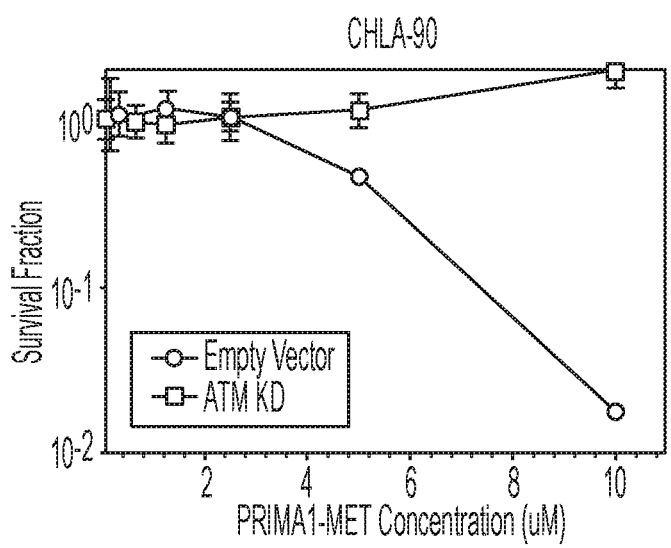

ALT Cells Acquire Resistance to PRIMA-1MET with Knockdown of DNA Damage Repair Kinase ATM FIGS. 20A and 20B illustrate data for cell line CHLA-90. shRNA knockdown of ATM in the ALT neuroblastoma cell line CHLA-90 led to hyper-resistance to PRIMA-1MET. We hypothesize this is due to the loss of constitutive activation of ATM in ALT positive cell lines which would trigger senescence and apoptosis once PRIMA-1MET refolds mutant p53 in the presence of ATM.

Figure 21A:
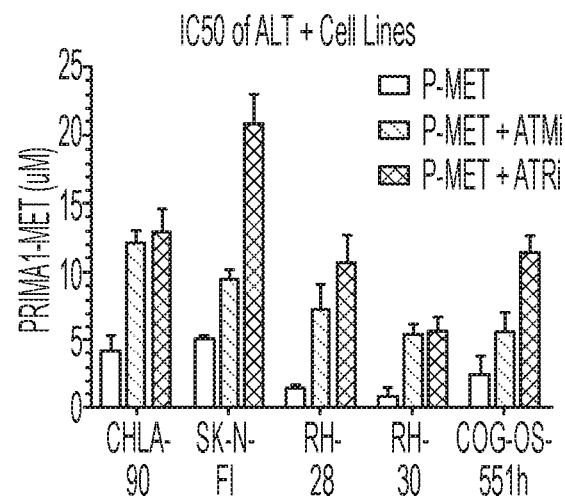
FIGS. 21A and 21B illustrate effect of inhibition of ATM or ATR kinase on sensitivity of ALT+ vs TERT+ (ALT-negative) using ATM kinase inhibitor (ATMi) or ATR kinase inhibitor (ATRi) it ALT+ and TERT+ cell lines.
Figure 21B:
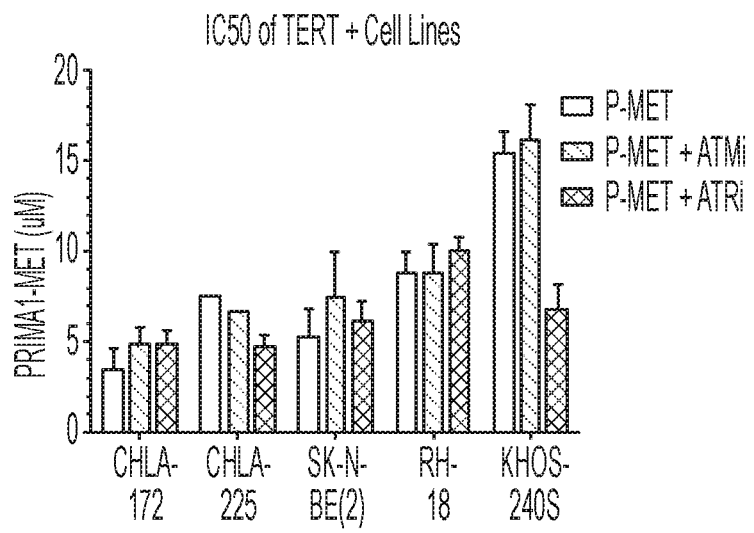

Inhibition of Both the ATM and ATR DNA Repair Kinases Leads to Resistance to PRIMA-1MET in Neuroblastoma, Rhabdomyosarcoma and Osteosarcoma Cell Lines FIGS. 21A and 21B illustrate inhibition of kinase inhibitors for ALT+ and TERT+ cell lines Kinase Inhibitors antagonize PRIMA-1MET in ALT+ cell lines. Presented as inhibitory+cytotoxic concentrations for 50% (IC50) of the cells, the IC50 greatly increases in ALT+ cell lines whereas there is little effect in TERT+ cell lines, likely because they don't have constitutive activation of the ATM and ATR kinases.

Figure 22A:
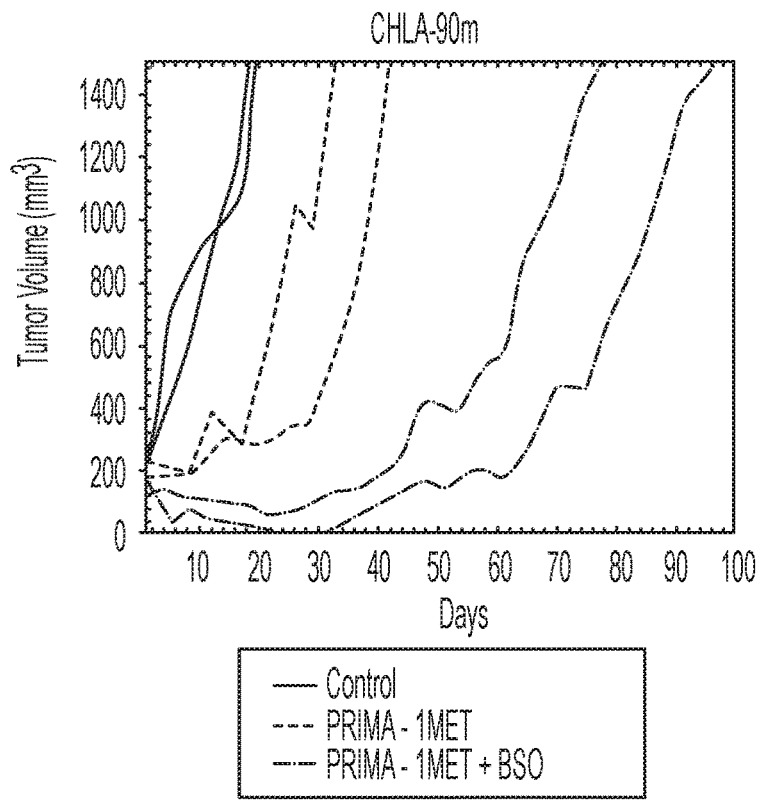
FIGS. 22A and 22B graphs tumor volume versus time for the ALT+ neuroblastoma xenografts CHLA-90m and COG-N-669x treated with PRIMA-1MET and BSO.
Figure 22B:
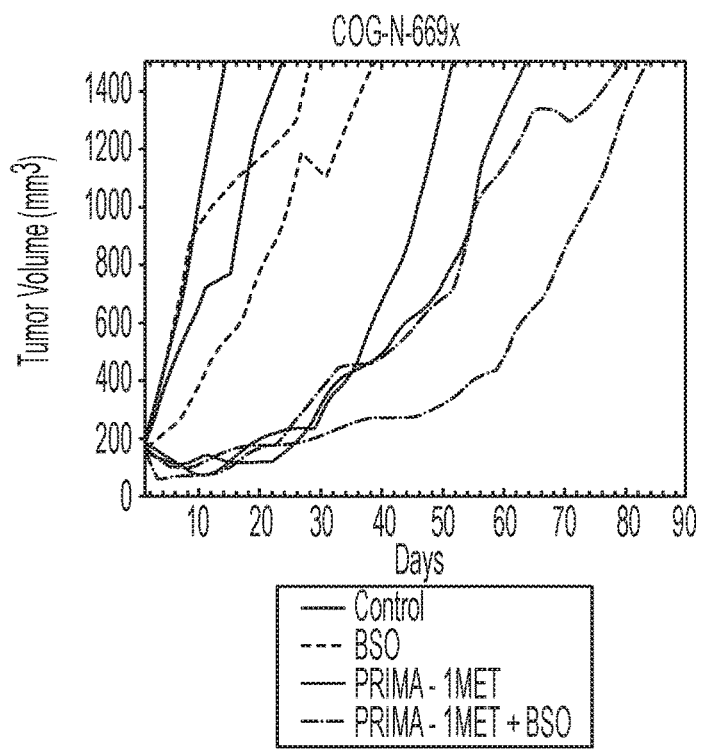

ALT Neuroblastoma Cell Lines CHLA-90m and COG-N-669x Xenografted into Immunocompromised Mice In Vivo using PRIMA-1MET with BSO FIGS. 22A and 22B are graphs tumor volume versus time for CHLA-90m and COG-N-669x. The neuroblastoma cell lines CHLA-90m and COG-N-669x were injected into athymic nude mice and drugged with PRIMA-1Met and BSO. We see a greater amount of activity with the single agent relative to the control and a highly significant difference in the double combination.

ALT Rhabdomyosarcoma Cell Line RH-30m In Vivo using PRIMA-1MET with Irinotecan

Figure 23A:
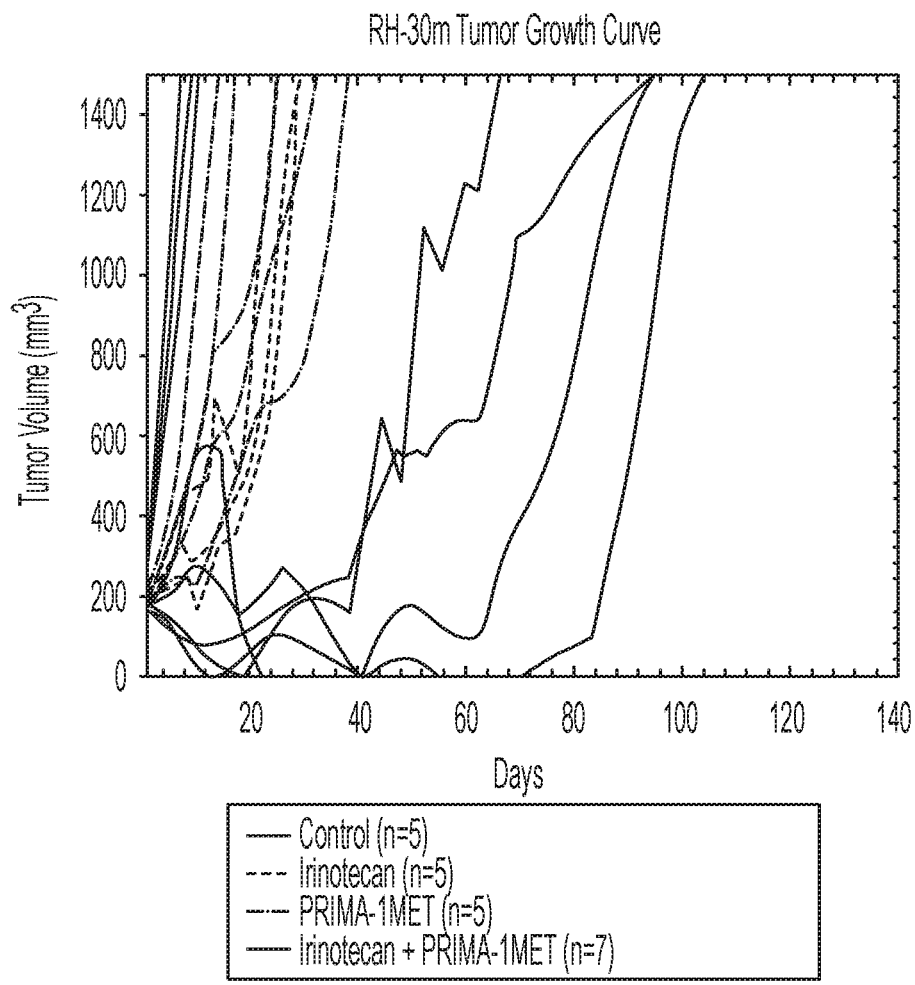
FIGS. 23A and 23B are graphs of tumor volume and survival % versus time for the ALT+ rhabdomyosarcoma xenograft RH-30m treated with PRIMA-1MET and Irinotecan compared to PRIMA1-MET or irinotecan as single agents.
Figure 23B:
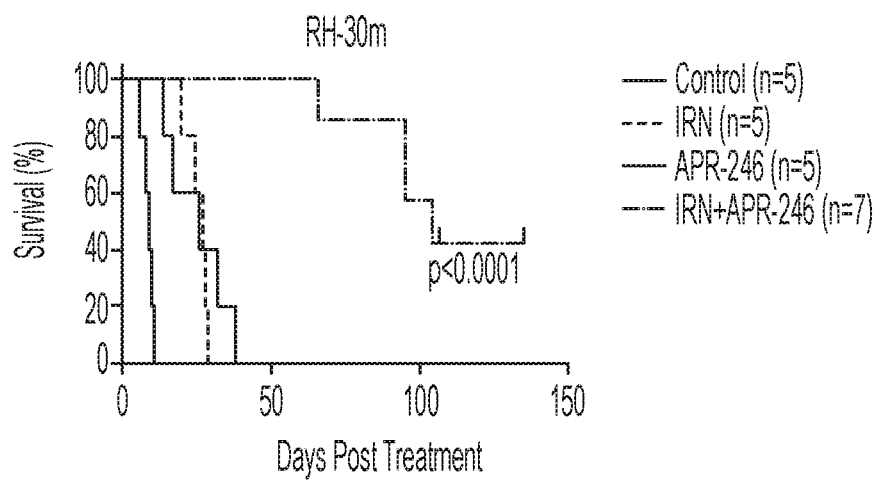

FIGS. 23A and 23B are graphs of tumor volume and survival % versus time for RH-30m. We grew the soft tissue rhabdomyosarcoma cell line RH-30m as xenografts in athymic nude mice and treated the mice with PRIMA-1MET and the topoisomerase DNA damaging agent irinotecan. Despite highly aggressive growth from the control mice, we observed that PRIMA-1MET significantly enhanced activity of irinotecan in this ALT rhabdomyosarcoma model.

What is claimed is:

1. A method of treating a cancer in a patient, the method comprising:
   obtaining a sample from the patient;
   detecting a presence of an alternative lengthening of telomeres (ALT) phenotype in the sample, wherein the ALT phenotype is associated with an ATRX mutation; and
   administering an effective amount of at least one of PRIMA-1 or APR-246 to the patient.

2. The method of claim 1, wherein the cancer is a lymphoma, a lung cancer, a breast carcinoma, a colorectal adenocarcinoma, or combinations thereof.

3. The method of claim 1, wherein the administering an effective amount of at least one of PRIMA-1 or APR-246 to the patient further comprises administering an anti-neoplastic agent.

4. A method of treating a cancer in a patient, the method comprising: administering at least one of PRIMA-1 or APR-246 to the patient, wherein the cancer comprises an alternative lengthening of telomeres (ALT) phenotype, and wherein the ALT phenotype is associated with an ATRX mutation.

5. The method of claim 4, wherein the cancer is a lymphoma, a lung cancer, a breast carcinoma, a colorectal adenocarcinoma, or combinations thereof.

6. The method of claim 4, wherein the administering at least one of PRIMA-1 or APR-246 to the patient further comprises administering an anti-neoplastic agent.

7. The method of claim 1, wherein the detecting comprises detecting the ATRX mutation.

8. The method of claim 1, wherein the ALT phenotype is associated with a DAXX mutation.

9. The method of claim 8, wherein the detecting comprises detecting the DAXX mutation.

10. The method of claim 1, wherein the detecting comprises utilizing a C-circle assay.

11. The method of claim 1, wherein the detecting comprises utilizing an ALT-associated promyelocytic leukemia (PML) bodies (APBs) assay, a large ultra-bright telomere fluorescence in-situ hybridization (FISH) assay, or combinations thereof.

12. The method of claim 1, wherein the administering comprises administering an effective amount of APR-246 to the patient.

13. The method of claim 4, wherein the ALT phenotype is associated with a DAXX mutation.

14. The method of claim 4, wherein the administering comprises administering APR-246 to the patient.

15. The method of claim 4, wherein the administering further comprises administering buthinonine sulfoximine to the patient.

16. The method of claim 1, wherein the cancer is associated with over-expressed phosphorylated (activated) ATM kinase.

17. The method of claim 16, wherein the detecting comprises detecting the overexpressed phosphorylated (activated) ATM kinase.

18. The method of claim 1, wherein the ALT phenotype is associated with a change in telomere length.

19. The method of claim 18, wherein the detecting comprises detecting the change in telomere length.

20. The method of claim 3, wherein the anti-neoplastic agent is a DNA damaging agent.

21. The method of claim 4, wherein the cancer is associated with over-expressed phosphorylated (activated) ATM kinase.

22. The method of claim 4, wherein the ALT phenotype is associated with a change in telomere length.

23. The method of claim 6, wherein the anti-neoplastic agent is a DNA damaging agent.

* * * * *